US012564656B2

(12) United States Patent
Erdi et al.

(10) Patent No.: US 12,564,656 B2
(45) Date of Patent: Mar. 3, 2026

(54) SPRAYABLE TISSUE ADHESIVE WITH BIODEGRADATION FOR WOUND TREATMENT

(71) Applicants:University of Maryland, College Park, College Park, MD (US); Children's National Medical Center, Washington, DC (US)

(72) Inventors: Metecan Erdi, Bethesda, MD (US); Peter Kofinas, N. Bethesda, MD (US); Omar B. Ayyub, Washington, DC (US); Anthony Sandler, Bethesda, MD (US); Michele Saruwatari, Washington, DC (US)

(73) Assignees: UNIVERSITY OF MARYLAND COLLEGE PARK, Bethesda, MD (US); CHILDREN'S NATIONAL MEDICAL CENTER, Washington, DC (US)

( * ) Notice: Subject to any disclaimer, the term of this patent is extended or adjusted under 35 U.S.C. 154(b) by 321 days.

(21) Appl. No.: 18/192,946

(22) Filed: Mar. 30, 2023

(65) Prior Publication Data
US 2023/0310695 A1 Oct. 5, 2023

Related U.S. Application Data

(60) Provisional application No. 63/362,192, filed on Mar. 30, 2022.

(51) Int. Cl.
| | |
|---|---|
| A61L 24/00 | (2006.01) |
| A61L 24/04 | (2006.01) |
| A61L 26/00 | (2006.01) |

(52) U.S. Cl.
CPC ......... *A61L 24/0026* (2013.01); *A61L 24/046* (2013.01); *A61L 26/0019* (2013.01); *A61L 26/0076* (2013.01); *A61L 2400/06* (2013.01)

(58) Field of Classification Search
CPC ...... A61L 24/00; A61L 24/04; A61L 24/0026; A61L 24/046; A61L 26/00; A61L 26/0019; A61L 26/0076; A61L 2400/06
See application file for complete search history.

(56) References Cited

U.S. PATENT DOCUMENTS 5,583,114 A * 12/1996 Barrows ............... A61L 24/046
424/193.1

* cited by examiner

*Primary Examiner* — Vi X Nguyen
(74) *Attorney, Agent, or Firm* — Hodgson Russ LLP

(57) ABSTRACT

Provided are compositions and methods that involve viscoelastic poly(lactide-co-caprolactone) (PLCL) mixtures for use in wound healing. The PLCL mixtures provide an improved anti-fibrotic yet tissue-adhesive polymer sealant. The PLCL mixtures can be applied to a variety of wounds arising from surgical and non-surgical tissue damage.

1 Claim, 17 Drawing Sheets
(16 of 17 Drawing Sheet(s) Filed in Color)

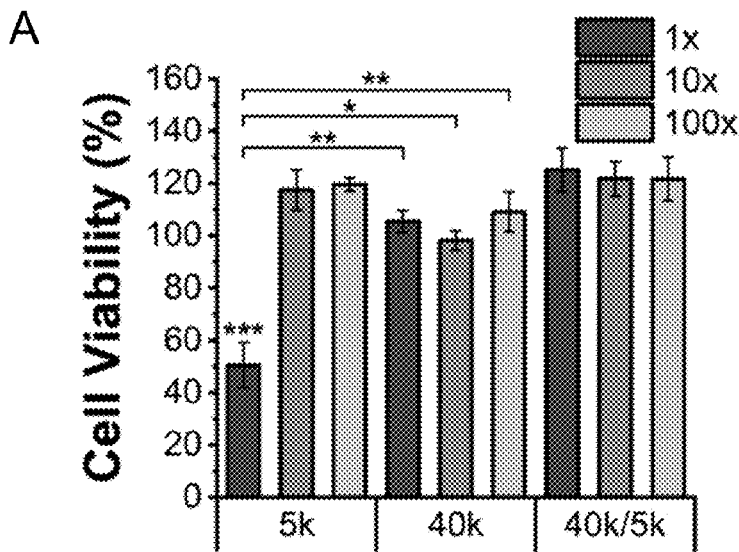

B

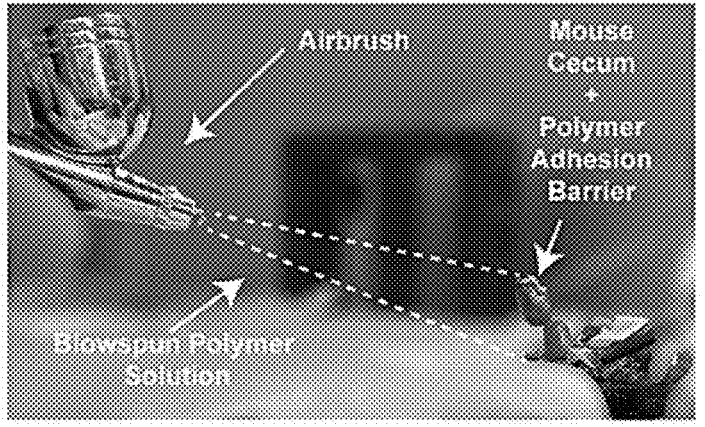

Mazuji-Modified Adhesion Severity Scoring System

| Grade | Description |
|---|---|
| 0 | No adhesions present. |
| 1 | Slight and small adhesions. Can be separated with blunt dissection, scattered throughout. |
| 2 | Moderately dense adhesions. Mostly separated with blunt dissection but requires sharp dissection in < 50% of adhered segments. Mild adhesions to abdominal wall. |
| 3 | Severe and continuous adhesions. Requires sharp dissection in more than 50% of the adhered segments. Strong adhesions to abdominal wall. |
| 4 | Dense and homogenous adhesions. Presence of serosal injury. Difficulty in lysis and identification of anatomy. |
| 5 | Presence of full-thickness injury. Excess perfusion upon lysis. Unable to clearly define anatomy. |

A

A

B

1

SPRAYABLE TISSUE ADHESIVE WITH BIODEGRADATION FOR WOUND TREATMENT

CROSS REFERENCE TO RELATED APPLICATIONS

This application claims priority U.S. Provisional Application No. 63/362,192, filed Mar. 30, 2022, the entire disclosure of which is hereby incorporated herein by reference.

STATEMENT REGARDING FEDERALLY SPONSORED RESEARCH OR DEVELOPMENT

This invention was made with government support under R01EB019963A awarded by the National Institutes of Health (NIH). The government has certain rights in the invention.

BACKGROUND

Abdominal adhesions are deposits of dense, connective scar tissue that form between organ surfaces as a result of uncontrolled fibrogenesis following surgery, trauma, inflammation, infection, or tissue ischemia.[1,2] Such uncleaved fibrous bridges are frequently reported in the human peritoneum following surgical interventions resulting in broad serous tissue injury (ex. abrasion, suturing), and are particularly common following abdominal surgeries such as laparotomy and appendicectomy.[3,4] Pathologic adhesion formation occurs due to an imbalance between the early fibrin deposition and degradation that occurs as part of healing after trauma, as well as the proximity of an injured surface to other structures.[5-7] In normal abdominal tissue healing, the entire injured surface heals uniformly, and affected cells secrete numerous pro-inflammatory cytokines, growth factors, and coagulants such as fibrin. Fibrous matrix deposition begins within 3 hours of tissue injury and increases until post-injury day 4 or 5, where it is then enzymatically degraded through fibrinolysis over the course of 1 week. In post-surgical adhesion formation, fibrin deposition outpaces fibrinolysis during the healing process and permanent connective adhesions are created between organs, with up to 93% of patients developing adhesions following operation in the abdomen or pelvis.[8-10] Such unsuppressed proliferation of fibrous tissue frequently causes small bowel obstruction, female infertility, or chronic abdominal or pelvic pain and is implicated in up to 60%, 40%, and 80% of cases, respectively.[11-14]

Removal of post-surgical adhesions through adhesiolysis can be attempted laparoscopically as to reduce frequency and severity in the abdominal cavity, but ultimately these procedures only have a ~70% success rate while also increasing the risk of new adhesion formation.[15] Treatment of small bowel obstruction accounts for up to 1% of all general surgical admissions, 3% of all laparotomies, over $2 billion in hospitalization and surgical expenditures annually, as well an approximated 900,000 days of inpatient care.[10,16-18] Because these surgical interventions to treat adhesions prove to be largely ineffective and costly, prophylactic barrier materials are needed that can prevent adhesions between organs before they form. Hydrogel-based adhesion barriers are the most widely adopted tool in surgical settings, but are difficult to apply, poorly adhesive to the target organ, and degrade too quickly to effectively prevent adhesions.[13]

Currently available clinical products to prevent adhesion formation include Seprafilm®, a pre-dried hydrogel film made of carboxymethylcellulose-hyaluronic acid that swells once in contact with aqueous abdominal fluid—and Interceed®, a woven cellulose mat. Both products act as solid barriers and physically prevent adhesions by separating injured mesothelial surfaces through interfacial lubrication imparted by their hydrophilic surface properties. Because they are pre-fabricated, such clinical products are brittle and difficult to apply, with limited flexibility when conforming to geometrically complex tissue surfaces. They also degrade rapidly in moist environments in the critical 5-day maturation period for adhesions, exhibit impeded wound healing, and inability to seal sites of injury, the combination of which limits their use in clinical practice.[19-24] Further, Seprafilm® undergoes a 90% loss in tensile strength within 30 minutes due to swelling of its carboxymethylcellulose-derived network, which renders it largely ineffective in the abdominal cavity where organs are in perpetual motion and tissue surfaces are routinely extending.[19-24] Recent biomaterials research efforts have recently focused on use of physically crosslinked hydrogels comprised of nanoparticles dispersed in a cellulose matrix.[25,26] However, they exhibit reduced flexibility and adherence to wet tissue, and also require an intricate syringe-based deposition technique. Other investigated hydrogel systems include ones forming chemical crosslinks to tissue in-situ via reactive end group chemistries, as the resultant material mimics biological tissue stiffness and thereby promotes biocompatible interfacing upon implantation.[27-29] However such materials frequently swell, causing undue pressure on surrounding tissue, and utilize crosslinking approaches that employ either toxic initiators or adhesive curing processes such as ultraviolet light and high temperature.[30,31] Previous work shows biocompatibility and efficacy of SBS-deposited polymer materials for in-vivo surgical applications including antimicrobial burn wound dressings[32], sealants for intestinal anastomosis[33-35], and hemostats for traumatic bleeding[36]. While stretchy, durable materials are desirable for high tissue adhesion, viscoelasticity and tunable biodegradation are necessary to provide a matrix that facilitates sufficient wound healing in a moist environment. For example, cohesively strong poly(lactic-co-glycolic acid) (PLGA) not only displays a lack of wet tissue adherence unless blended with an additional adhesive component, but also induces abdominal adhesions in a clinical mouse model over a 10 day time course.[37] Such shortcomings are a result of a near 0% loss in polymer mass and remaining polymer providing a template for fibrous tissue growth. Thus, there is an ongoing and unmet need for improved compositions and methods for use in treating wounds. The present disclosure is pertinent to this need.

BRIEF SUMMARY

The present disclosure provides in embodiments an tissue wound barrier that is sprayable, tissue adhesive to only a target organ or other tissue, degradable at the same rate as the tissue wound healing process, and does not impede wound healing. Non-limiting embodiments are demonstrated using solution blowspinning (SBS) of dry, conformal polymer fibers with controllable surface erosion. Through blending of fast degrading low molecular weight and slow degrading high molecular weight surface eroding polymers at defined ratios, the disclosure provides in non-limiting embodiments sprayable fiber mats with linear biodegradation profiles tuned to a clinically relevant rate.

This disclosure also provides an analysis of the effect of different molecular weight blends of PLCL on biodegradation profile, cohesive strength, and tissue adhesion, followed by implementation into a preclinical mouse model of abdominal adhesions. Multiple low and high molecular weight combinations of poly(L-lactide-co-caprolactone) (PLCL) were analyzed to modulate surface erosion rate and determine its subsequent effect on adhesion prevention to arrive at an embodiment in which a mixture of 40 k and 5 k poly PLCL performed that exhibits a variety of improved properties, as further described below. Since degraded fragments of PLCL continually erode from the surface, PLCL is demonstrated herein to act as an improved wound healing material with a degradation profile that is tuned to coincide with the progression of scar tissue formation (see, for example, FIG. 1). An eroding surface mitigates cell adhesion and fibrin deposition, which are, for example, required for formation of adhesions.[39,40] In embodiments that are described in more detail below, the barrier itself is tuned to retain the described mechanical properties at the application site, and occludes atypical deposition of fibrous, vascular scar tissue until the target wound has healed. In embodiments the disclosure provides a balance between the presence of wound healing components through kinetic control of degradation, as well as cohesive and adhesive strength through facile tuning of high and low molecular weight ratios. Poly(lactic-co-glycolic acid) (PLGA) was used as a non-limiting example of a bulk degrading control that undergoes minimal erosion during the adhesions-forming period.

As described in the Examples below, in-vitro biodegradation and mechanical testing techniques were used to determine a preferred composition of a PLCL molecular weight blends for adherence to wet tissue, biocompatibility, and inhibition of scar formation. PLCL blends were tested in an in-vivo mouse cecal ligation model via assessment of adhesion severity and subsequent immunological analysis to demonstrate the benefits of the described spray deposited, wet tissue conforming, tissue wound barrier material. Accordingly, the disclosure provides in an embodiment a method comprising contacting a tissue wound with a composition comprising a mixture of 40 k and 5 k poly PLCL to thereby promote healing of the tissue wound. In embodiments, the 40 k and 5 k PLCL are present in a 70:30 mass ratio, respectively. In embodiments, a described composition is free of PLGA, or poly(ethylene glycol) (PEG), or nanoparticles, or a combination thereof. In one embodiment, the composition when in contact with a tissue wound consists essentially of the 70:30 mass ratio mixture of 40 k/5 k PLCL. In embodiments the composition that is in contact with the tissue wound may be present as a solid adhesive. The compositions and methods are suitable for use with a variety of tissue wounds, including but not necessarily limited to a surgical wound, a non-surgical laceration, a tissue tear, a tissue puncture, a tissue abrasion, a tissue ulceration, a heat burn, a chemical burn, or a pressure sore. In embodiments a surgical wound that is treated according to this disclosure is a post-operative abdominal incision.

Compositions and methods of this disclosure include those described above, and compositions and uses thereof, wherein the compositions comprise the described mixtures of 40 k and 5 k PLCL, compositions that consist essentially of the described mixtures of 40 k and 5 k PLCL, and compositions that consists of the described mixtures of 40 k and 5 k PLCL.

The disclosure also provides systems comprising a container containing a composition comprising a 70:30 mass ratio mixture of 40 k/5 k PLCL, which may be provided as a 70:30 mass ratio, respectively. The container may be in fluid communication with an application device, such as a solution blow spinning device, such as an airbrush.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
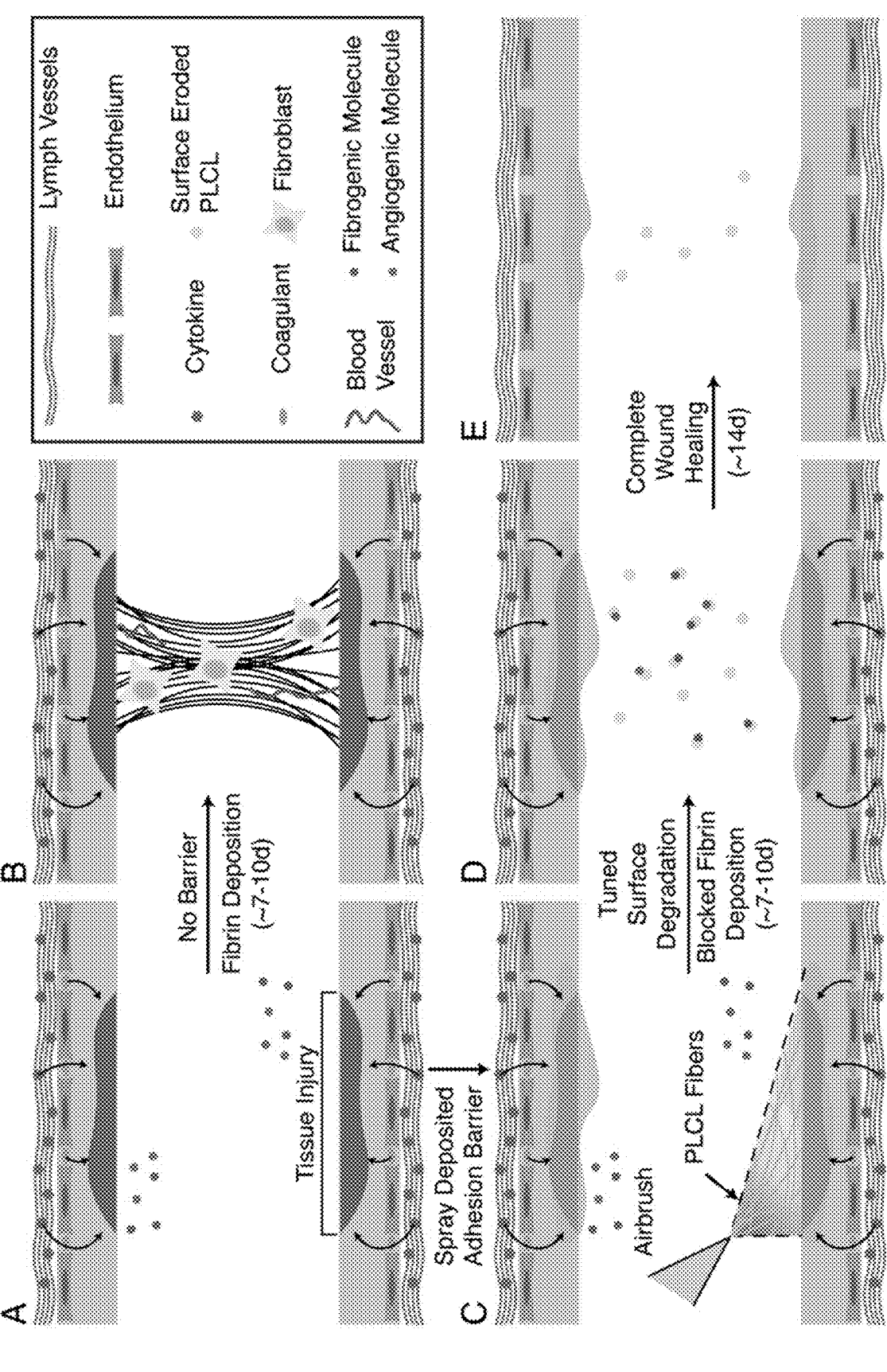
FIG. 1. Illustration of adhesion formation in the presence of no barrier and treatment via surface eroding polymer adhesion barrier. (A) Formation of adhesions is a consequence of reduced fibrinolytic activity following ischemic mesothelial tissue injury, (B) leading to deposition of connective wound healing tissue. (C) Our poly(L-lactide-co-caprolactone) (PLCL) molecular weight blends yield a viscoelastic, wet tissue adhesive rapidly deposited via solution blowspinning (SBS) for application and retention in the abdominal cavity, while also presenting a surface erosion degradation mechanism apt to (D) prevention of adhesion formation and (E) wound healing.

Unless defined otherwise herein, all technical and scientific terms used in this disclosure have the same meaning as commonly understood by one skilled in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof.

As used in the specification and the appended claims, the singular forms "a" "and" and "the" include plural referents unless the context clearly dictates otherwise. Ranges and other values may be expressed herein as from "about" or "approximately" one particular value, and/or to "about" or "approximately" another particular value. When values are expressed as approximations by the use of the antecedent "about" or "approximately" it will be understood that the particular value forms another embodiment. The term "about" and "approximately" in relation to a numerical value encompasses variations of +/−10%, to +/−1%.

The disclosure provides compositions and methods for use in treating wounds. All methods of making the compositions, materials, and products described herein are included in the disclosure. The disclosure includes all methods and materials described herein, and all mechanical, physical and biological properties of the material and results from using the same, including but not necessarily limited to any tensile property, including but not necessarily limited to tensile stiffness and tensile elongation, wet tissue adherence, tensile elasticity, degradation characteristics, erosion characteristics, contact angle measurements, viscosity, adhesive strength, cohesive strength, yield stress, resistance to shear forces, cell viability, reduction of indicia of inflammation, including but not limited to reduction of expression of inflammation related genes, and any measurement of wound healing, including effects of the described compositions on inhibition of scar tissue formation, and complete wound healing such as evidenced in a cecal ligation mouse model.

In embodiments the disclosure provides a method comprising contacting a tissue wound with a composition comprising a mixture of 40 k and 5 k poly PLCL to thereby promote healing of the tissue wound. In embodiments the 40 k and 5 k PLCL are present in a 70:30 mass ratio, respectively. For instance, if the composition contains 70 grams of the 40 k PLCL then the composition contains 30 grams of the 5 k PLCL. When a described composition is prepared and ready for use in treating a wound, the composition can be free of PLGA, or poly(ethylene glycol) (PEG), or nanoparticles, or any combination thereof. The compositions may also be free of any acrylates, including but not limited to cyanoacrylate glue. The compositions may also be free from carboxymethylcellulose and hyaluronic acid. The composition may comprise, consist essentially of, or consist of the 40 k and 5 k PLCL mixture, wherein one or more solvents used to produce the composition, such as ethyl acetate, may initially be present but evaporate when applied to a tissue wound. As such, a described composition may comprise, consist essentially of, or consist of the stated the 40 k and 5 k PLCL mixture when ready for use or when in contact with a tissue wound. In embodiments, prior to contacting a tissue with the composition, the composition may comprise a solvent, such as ethyl acetate. Thus, before use, the composition may comprise, consist essentially of, or consist of the 40 k and 5 k PLCL and at least some solvent. In an embodiment the composition consists essentially of the 40 k and 5 k PLCL and a trace amount of solvent. After application to the wound the composition may be in the form of a solid adhesive.

Methods for applying wound healing materials to wounds are known in the art and can be adapted for use in the described methods. In one embodiment, contacting a tissue wound comprises spraying the composition onto a wound. In an embodiment solution blow spinning (SBS) of the composition onto the wound is performed.

Contacting the tissue wound with a described composition inhibits formation or severity of scar tissue. A non-limiting example of scar tissue to which the present disclosure pertains is referred to herein as an "adhesion"—the meaning of which is understood in the art. In embodiments, the compositions and methods of this disclosure are used to inhibit the development or severity of adhesions, including but not necessarily limited to abdominal adhesions. In embodiments, the compositions and methods of this disclosure are used to inhibit the development of or prevent formation of a hypertrophic scar or a keloid.

In embodiments, an effective amount of a described composition is used. In embodiments, an effective amount is an amount that inhibits development of one or more characteristics of scar tissue, such characteristics being well known in the art. Non-limiting examples of scar tissue characteristics include replacement of normal tissue with fibrous tissue having at least a different collagen arrangement relative to normal tissue, such as cross-linked and/or aligned collagen typically present in scar tissue. An effective amount may also maintain or reduce loss of elasticity of the wounded tissue. An effective amount can be selected by the individual physician in view of the wound to be treated. Dosage and administration can be adjusted to provide sufficient levels of the composition to maintain the desired scar-inhibiting effect. Additional factors that may be taken into account when determining an effective amount include the location, size, and severity of the wound, as well as the age and size and type of the individual being treated. A non-limiting example of an effective amount is approximately 0.5 mL of a described composition for each 1 cm of a wound. The composition is generally applied after the wound has been closed using any suitable wound closing device, including but not necessarily limited to sutures and staples.

In embodiments, a wound that is treated according to the disclosure comprises damage to an internal tissue of the body, including but not necessarily limited to tissue of an internal system or organ, including but not necessarily limited to any part of the digestive system, such as the esophagus, abdominal cavity, stomach, large and small intestines, and colon. In embodiments, the wound is a surgical wound, a non-surgical laceration, a tissue tear, a tissue puncture, a tissue abrasion, a tissue ulceration, a heat burn, a chemical burn, or a pressure sore. Thus, in embodiments, the disclosure pertains to a wound where a tissue of an individual is cut, wherein the cut can include but is not necessarily limited to an incision made with a sharp object, such as a surgical scalpel or other cutting implement, or a surgical laser. In embodiments a wound that is treated according to the disclosure thus comprises tissue damage created intentionally or is incidental to a medical procedure. In embodiments, the wound is not created by or during a medical procedure, and instead results from another source of trauma, such trauma to tissue by accidental contact with a heated surface or chemical, or exposure to radiation, or an accidental or an intentional non-medical circumstance whereby tissue is cut or punctured or avulsed, including but not necessarily limited to tissue trauma resulting from participation in sporting events, industrial accidents, household accidents, automobile accidents, natural disasters, and acts of violence or war.

In embodiments, the present disclosure provides cosmetic or pharmaceutical or nutraceutical compositions comprising a cosmetically or pharmaceutical or nutraceutical effective amount of a composition described herein.

In embodiments, the compositions and methods of the disclosure are suitable for prophylaxis and/or therapy for a wound of any human or non-human animal, such as any mammal, including human and non-human mammals, and is thus considered to be suitable for use in human and veterinary medicine.

Any result obtained using a composition and method described herein can be compared to any suitable reference, such as a known value, or a control sample or control value, suitable examples of which will be apparent to those skilled in the art, given the benefit of this disclosure. In non-limiting embodiments, use of a described composition provides an improved result relative to a result obtained using a composition that comprises on type or a combination of different forms of PLCL and at least one of poly(lactic-co-glycolic acid) (PLGA), poly(ethylene glycol) (PEG), or nanoparticles. In embodiments, a described Mazuji-derived scoring rubric of clinical severity of adhesions may be used to identify an improved result from use of a described composition, relative to use of a previously known composition. In an embodiment, using a composition and method described herein provides an improved wound healing result relative to use of Seprafilm®. In an embodiment use of a described composition provides an improved reduction in fibrous tissue in scar tissue, and/or maintains or reduces loss of elasticity of the wounded tissue. In embodiments, use of a described composition provides at least one of: an improved biodegradation profile, improved cohesive strength, or improved tissue adhesion (i.e., adherence to tissue), relative to a reference.

The described compositions may or may not be used in conjunction with bandages, wound dressings, compresses, fabric meshes, sutures, or any other product or device intended to treat, close, protect or otherwise inhibit the formation of scar tissue.

In another example the disclosure provides a system comprising a container containing a composition comprising a 70:30 mass ratio mixture of 40 k/5 k PLCL, and wherein the 40 k and 5 k PLCL are present in a 70:30 mass ratio, respectively. Any suitable container may be used, non-limiting examples of which include one or more closed or sealed vials, bottles, blister packs, or single-use or reusable cartridges, and the like. One or more containers may be in fluid communication with a suitable device for application of a described composition to a wound, such as a solution blow spinning device, which can be provided in the form of an airbrush. In embodiments, the system includes packaging and printed material. The printed material can be part of the packaging, or it can be provided on a label, or as paper insert or other written material included with the packaging. The printed material provides information on the contents of the package, and instructs a user how to use the package contents.

The analysis is described in the following Examples, which are not meant to limit the disclosure.

Example 1—Biodegradation, Mechanical Properties, and Biocompatibility of Neat and Blend PLCL Degradation of surface eroding PLCL blends was studied by immersing samples in 37° C. water. Samples were then removed at select time intervals, and following a vacuum dry step, measured for mass loss, and then prepared for both molecular weight distribution analysis via gel permeation chromatography (GPC) and tensile stiffness measurements via dynamic mechanical analysis (DMA).

Figure 2:
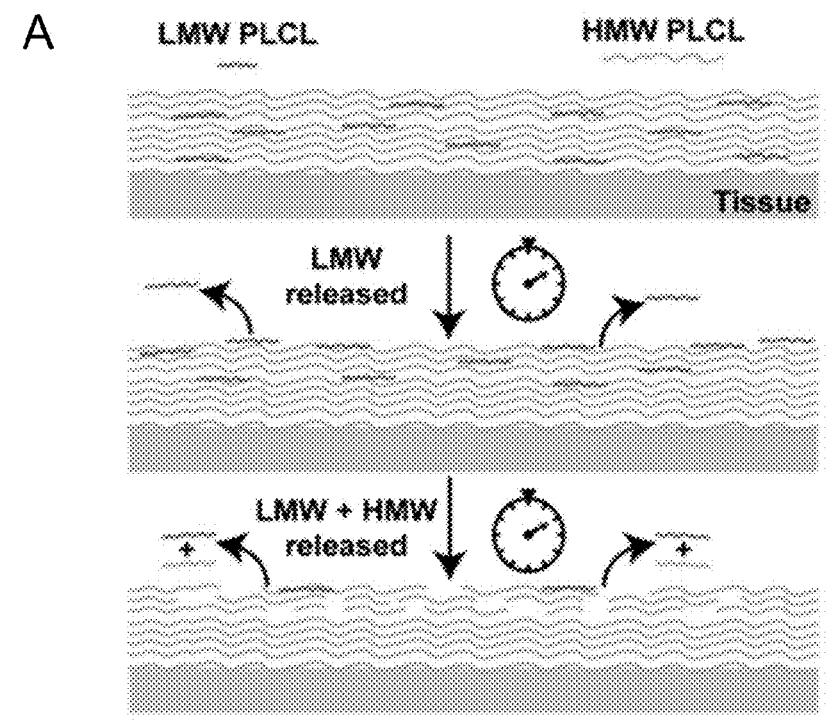
FIG. 2. Shown are (A) schematic of degradation mechanism for poly(L-lactide-co-caprolactone) (PLCL) via polymer surface erosion. (B) Advancing water droplet contact angle of neat and blend PLCL at start and end of in-vitro degradation. (C) Mass loss for neat and blended PLCL. (D) Number average molecular weight and (E) overall distributions for PLCL blends (i), (ii), (iii) during in-vitro degradation. HMW="high" molecular weight. Blending of different molecular weights allows for tunable degradation with rapid linear degradation in the first several days for 80 k/5 k and 40 k/5 k blends. LMW="low" molecular weight. (')=HMW peak of blend. (")=LMW peak of blend. Data is plotted as mean±s.e. * p<0.05; p<0.01; *p<0.001.
Figure 2:
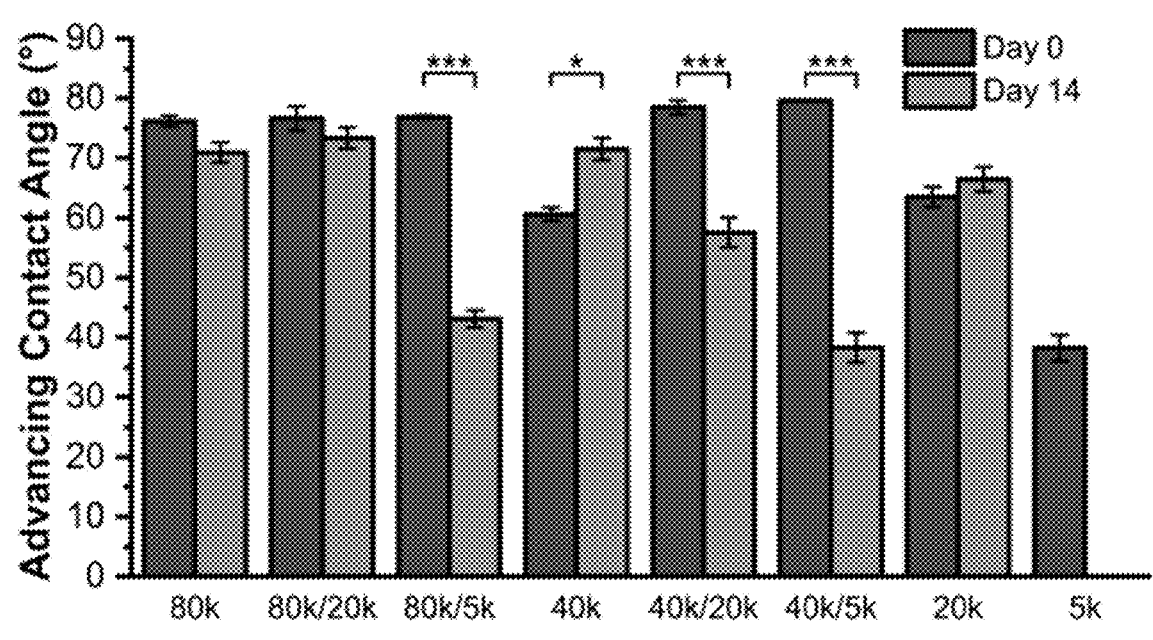
Figure 2:
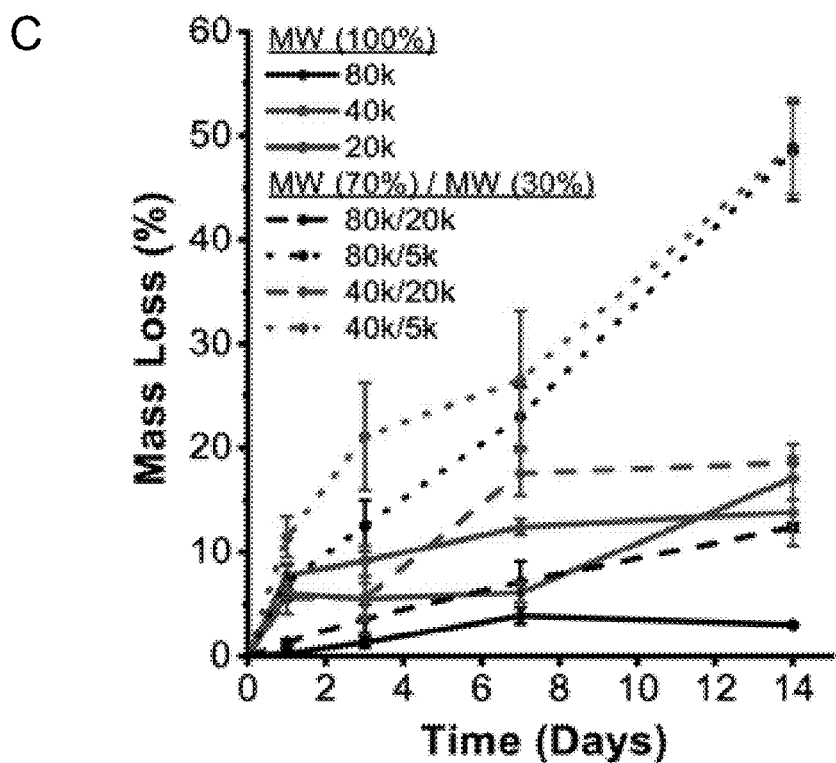
Figure 2:
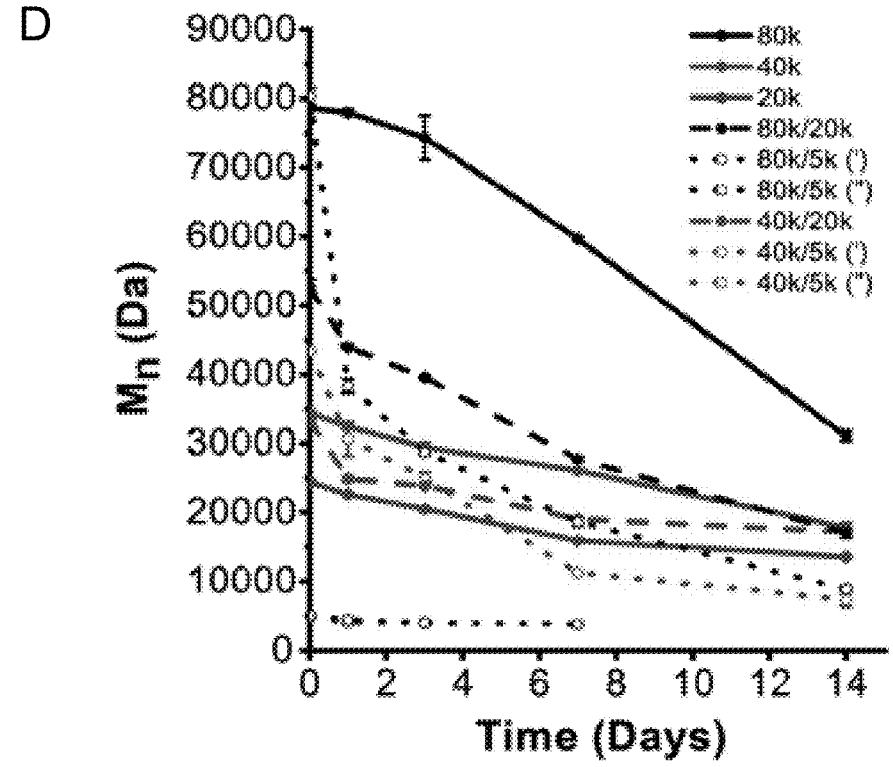
Figure 2:
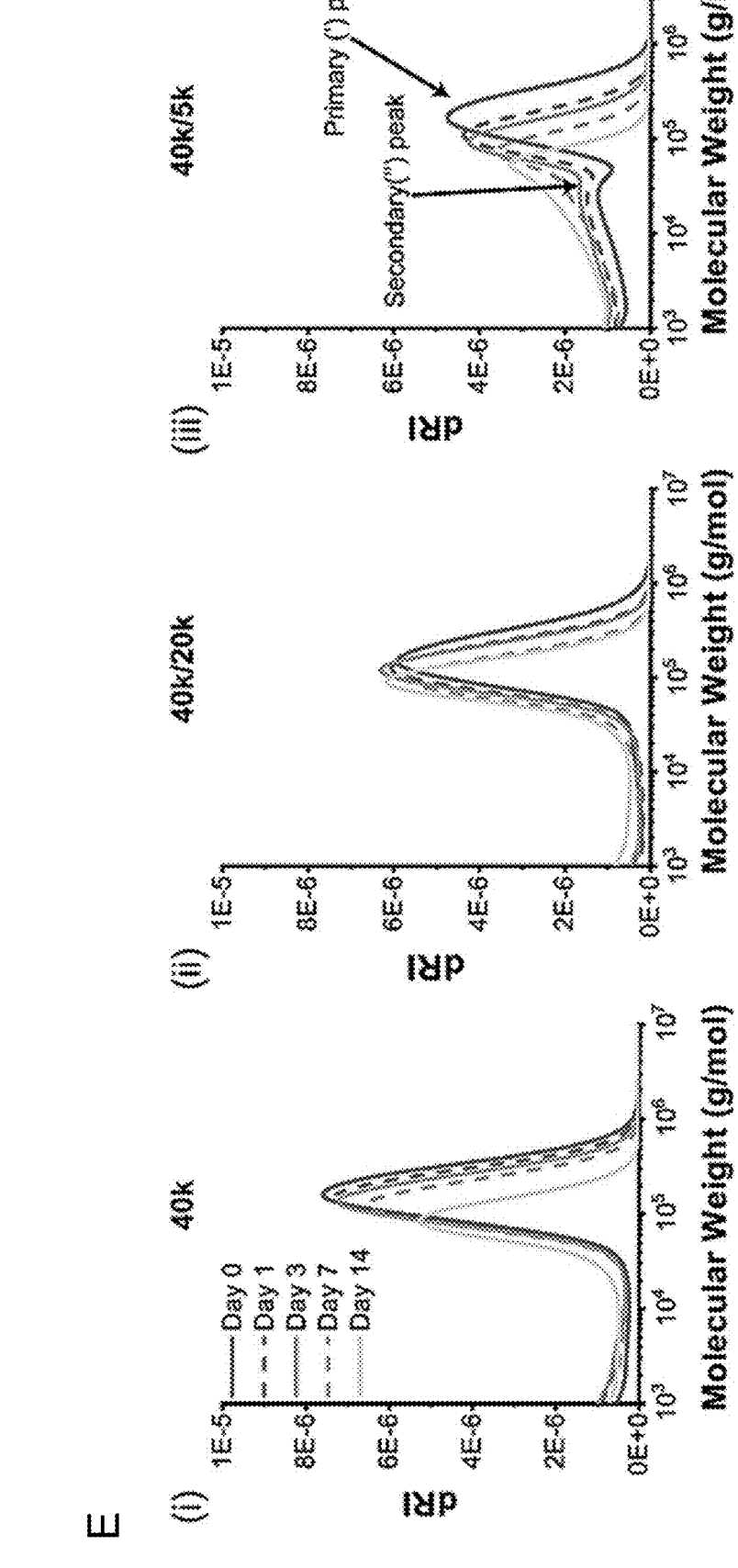

Molecular weight blends of surface eroding polymers present an opportunity to finely tune composite degradation profile due to the faster erosion rate of low molecular weight (LMW) chains. LMW chains in the initially fabricated fiber mat accumulate at the material surface and decrease the contact angle of blends over time (FIG. 2A-B). Contact angle measurements for neat HMW PLCL are unchanged over 14 days, but they decrease significantly when blended with 5 k PLCL, indicating the presentation and erosion of LMW chains with hydrophilic endgroups at the fiber mat surface.

Figure 6:
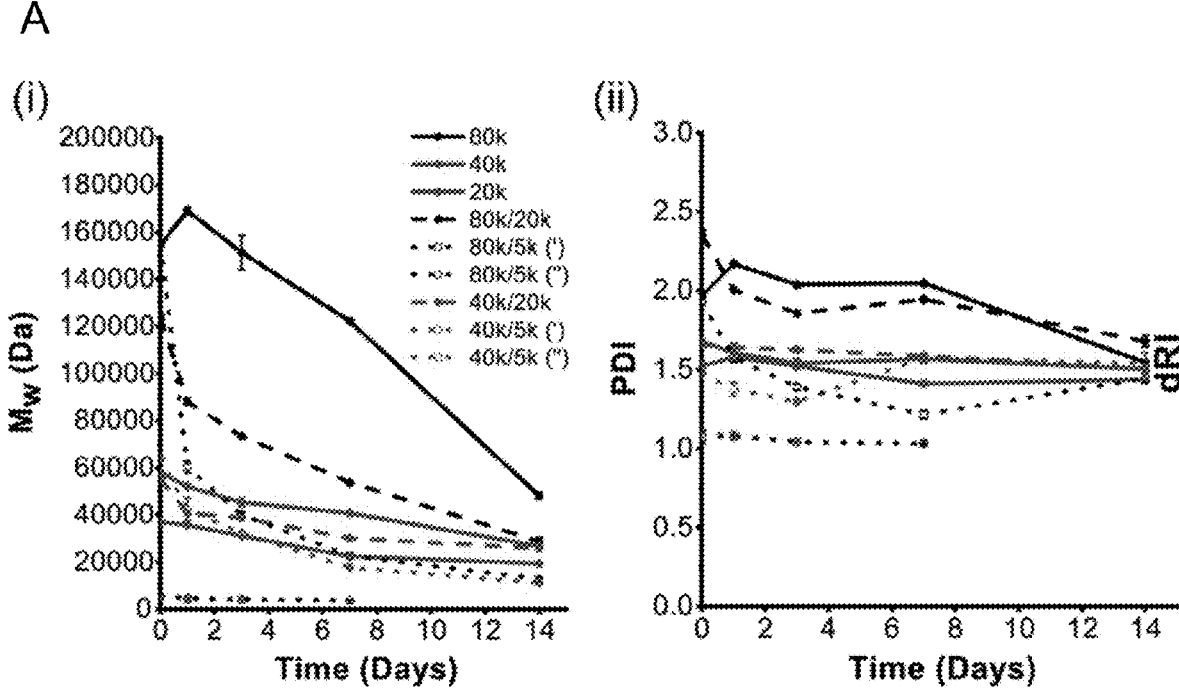
FIG. 6. Graphs showing (A) (i) weight average molecular weight and (ii) polydispersity index (PDI) for neat and blended poly(L-lactide-co-caprolactone) (PLCL) during in vitro degradation. (B-C) Overall distributions for PLCL blends (i), (ii), (iii) during in vitro degradation. (')=HMW peak of blend. (")=LMW peak of blend. Data is plotted as mean±s.e.
Figure 6:
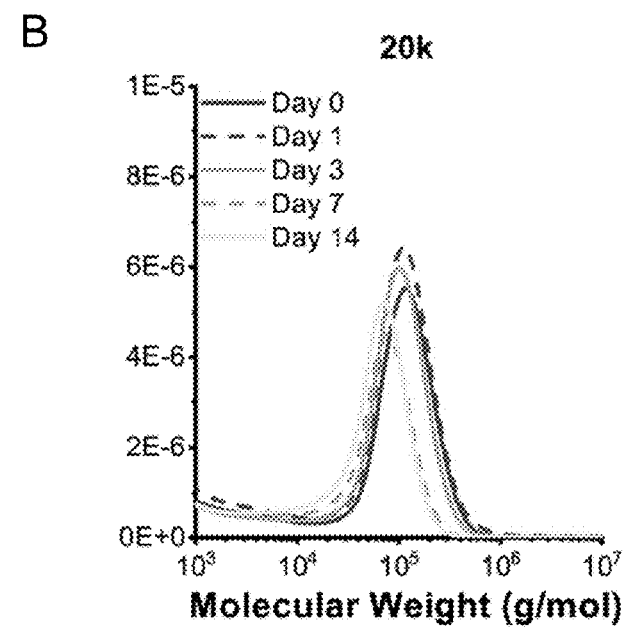
Figure 6:
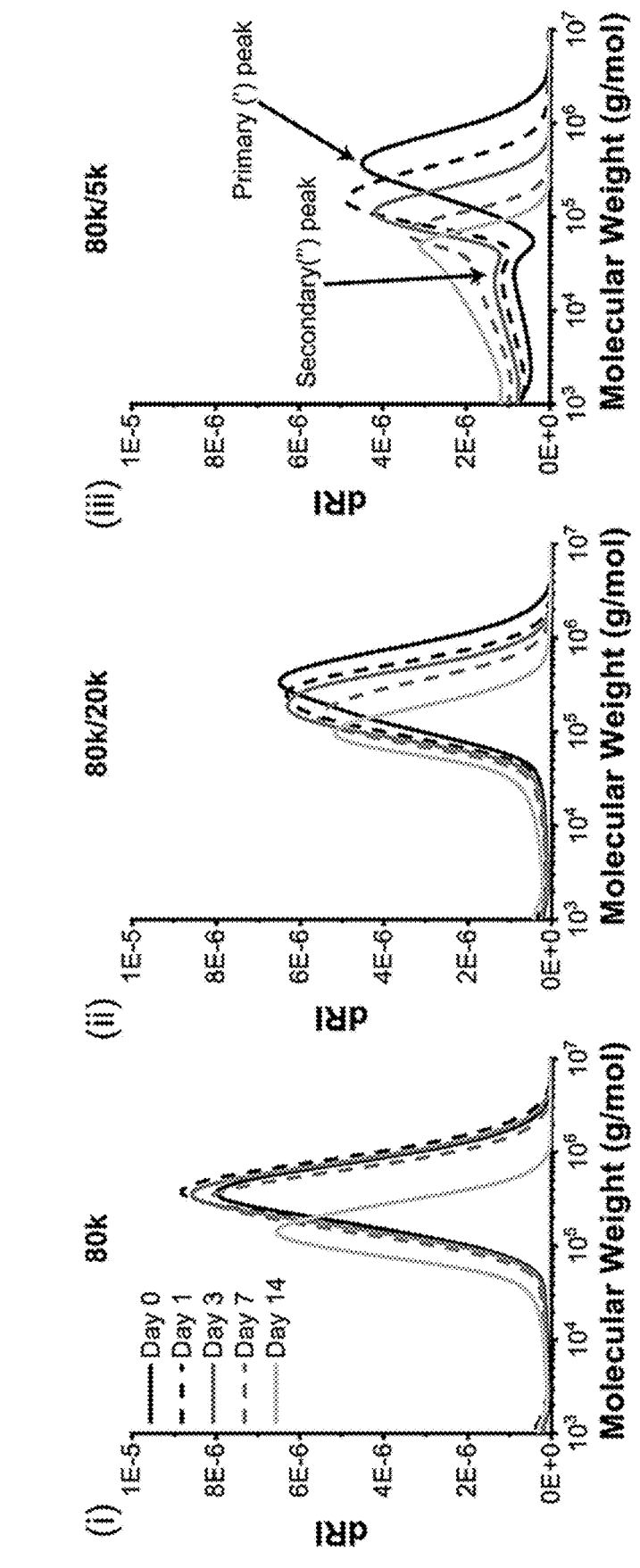

Adhesions form within 5-7 days and then mature over two weeks. A preferred material prevents contact between surfaces during the initial stages of fibrin deposition and persists until the injured mesothelium is healed. Blending HMW 40 k or 80 k PLCL with LMW 5 k PLCL at a 70:30 ratio results in a linear degradation profile for up to 14 days (~50% mass loss) (FIG. 2B) while also displaying distinct bimodal molecular weight distributions in GPC not presented in other blends and neat compositions (FIG. 2C-D, FIG. 6). As these particular blends begin to degrade and decrease in molecular weight, there is a shift to a unimodal distribution with a high PDI (~3) due to the presence of 5 k PLCL as synthesized, along with degraded portions of 40 k or 80 k PLCL. Since all other blend compositions yield only 5-20% mass loss and plateau in later stages, without intending to be constrained by any particular interpretation, it is considered that 40 k/5 k and 80 k/5 k PLCL blends equivalently release short chain fragments from the polymer surface over a 14d treatment period for adhesions. The fast, linear erosion rate decreases accumulation of fibro- and angio-genic molecules, such as fibrinogen and vascular endothelial growth factor (VEGF), reducing scar tissue formation on healing mesothelium.

Blending either LMW 5 k or 20 k PLCL in a HMW 40 k or 80 k PLCL matrix greatly promotes tensile elasticity as both are near (20 k) or below (5 k) entanglement molecular weight, whilst presenting viscous behavior that permits flow upon application of an external force. 40 k/5 k and 80 k/5 k PLCL blends in particular display improved adhesive strength to tissue versus their neat 40 k or 80 k PLCL compositions, as the 5 k component allows the sealant to spread across a given surface under application of pressure. Adhesion to a surface under these conditions is facilitated through physical mechanisms of polymer chain entanglement with complex tissue topography and short-range interactions (ex. Van der Waals) with surface molecules as facilitated through the viscoelastic nature of our adhesive.[41-43]

Figure 7:
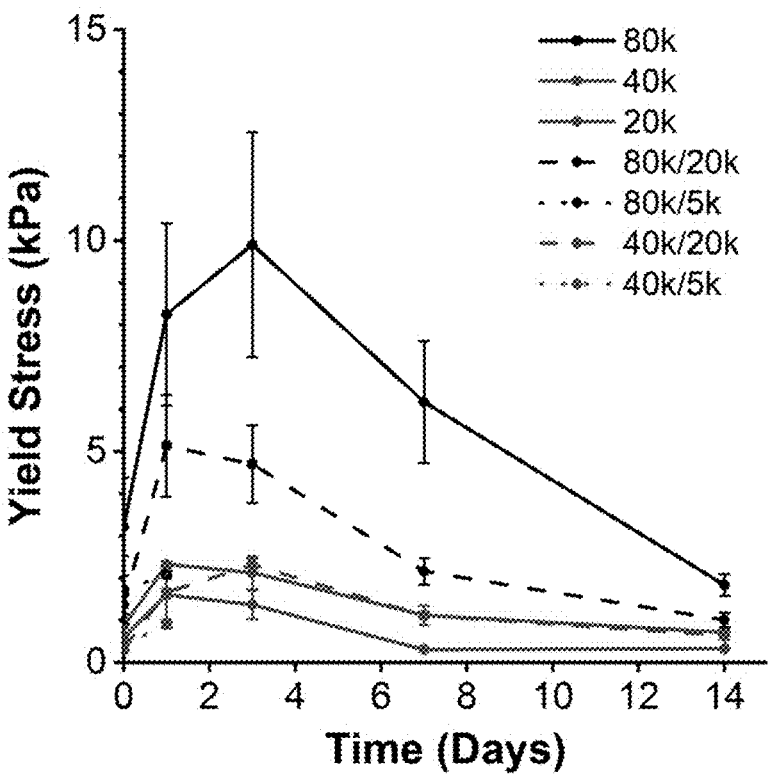
FIG. 7. Yield stress values of neat and blend poly(L-lactide-co-caprolactone) (PLCL) during in vitro degradation. Data is plotted as mean±s.e.

Blending 5 k or 20 k PLCL produces materials with decreased stiffness (FIG. 3A) and values of yield stress (FIG. 7) versus neat HMW compositions during in-vitro degradation. Yield strain values remain in the same order of magnitude no matter the compositions, indicating similarity in elastic range across all compositions and time points (FIG. 3B). Blends of PLCL with 5 k or 20 k components exhibit augmented pull-apart adhesion strength versus respective neat HMW compositions on not only dry porcine skin, but also internal wet porcine intestine (FIG. 3C). Such an improvement is due to an adjusted balance between cohesive strength and adhesive strength. While neat 20 k PLCL displays significantly increased adhesive strength versus other compositions in wet tissue on porcine intestine, the lack of cohesive strength elucidated by tensile stiffness measurements, as well as an unfavorable non-linear degradation profile (FIG. 2C), make it a poor adhesion barrier material candidate. The equivalent biodegradation rate over 14d (FIG. 2C) for 40 k/5 k PLCL, coupled with superior dry and wet tissue adhesion strength (FIG. 3C), demonstrates improved properties of this embodiment.

Figure 4:
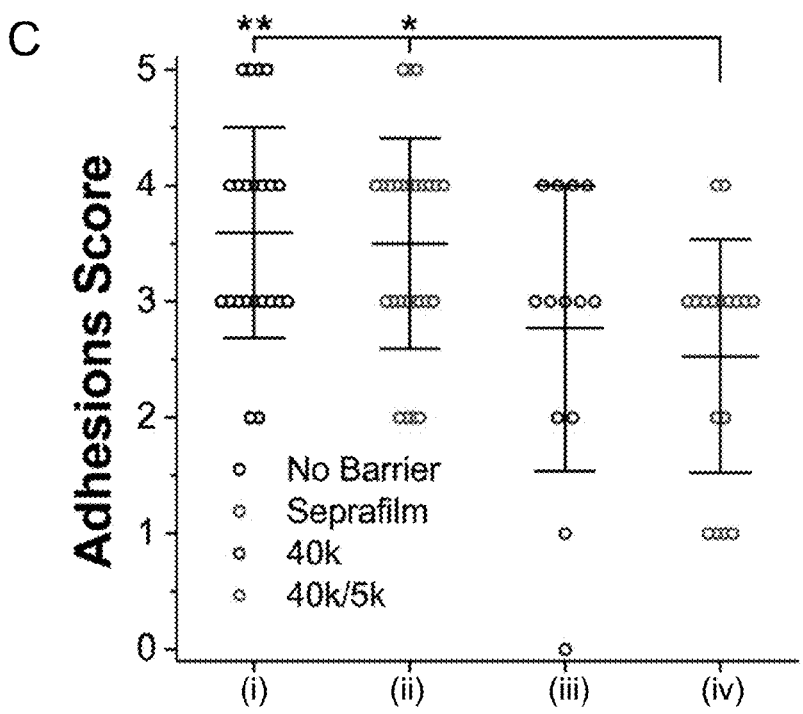
FIG. 4. Graph showing (A) L929 mouse fibroblast cell viability (versus media only control) of neat and blended poly(L-lactide-co-caprolactone) (PLCL) for 1×, 10×, and 100× dilutions of treatment media. (B) Application of polymer adhesion barrier during mouse cecal ligation and Mazuji-derived adhesion scoring rubric used in clinical assessment. (C) Clinical scores and (D) gross pathology for (i) no barrier, (ii) Seprafilm®, and (iii and iv) PLCL treated groups post-cecal ligation at t=7 days. PLCL treatment groups showed increased significance versus empty and clinical controls in reducing adhesions severity. Data is plotted as mean±s.e. Asterisks indicate statistical significance: * p<0.05; p<0.01; *p<0.001 (5 k PLCL versus unmarked groups in cell viability).
Figure 4:
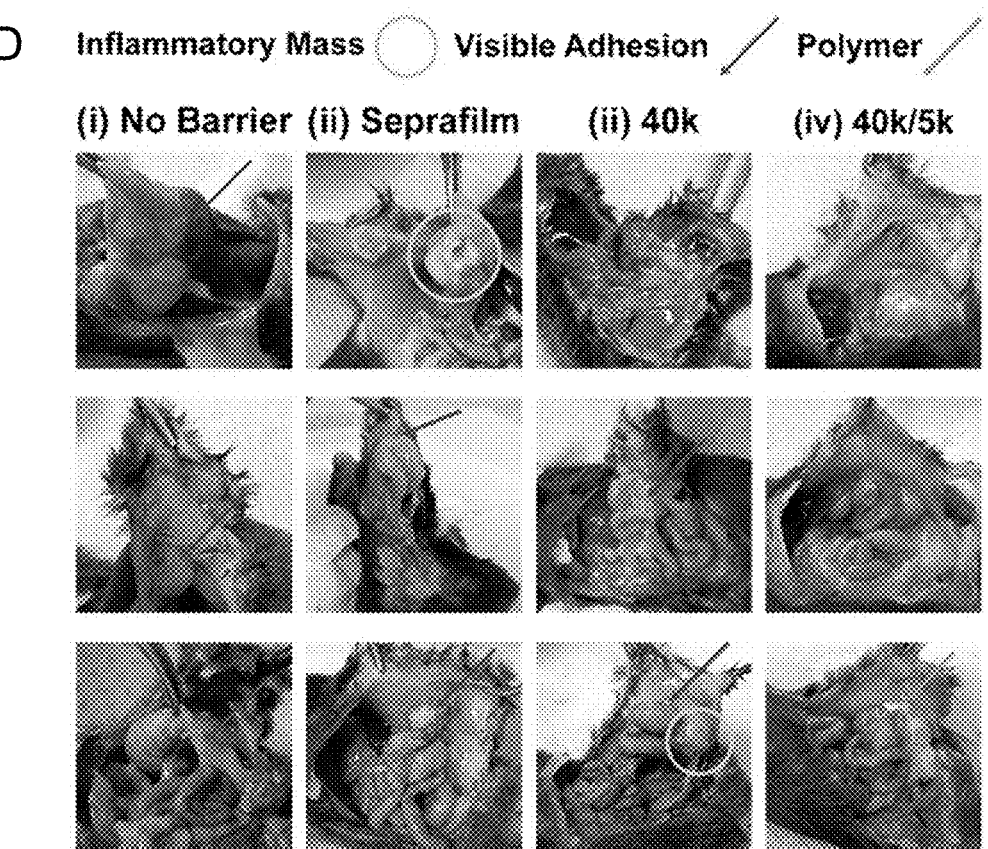

Example 2—In-Vivo Efficacy in a Mouse Model of Abdominal Adhesions and Wound Healing Below entanglement molecular weight polymers (~1 kDa) formed in-vivo can exhibit toxic effects due to an ability to disrupt cell membrane integrity.[44] We therefore assessed toxicity prior to in-vivo implantation of 5 k PLCL in either neat or blend compositions. L929 mouse fibroblasts were treated with supernatant of degraded polymer. Neat 5 k PLCL significantly reduced cell viability (~50%) of L929 mouse fibroblasts at 1×concentration, while neat 40 k and blended 40 k/5 k PLCL compositions had no effect on cell viability at all dilutions (FIG. 4A). This indicates that 40 k/5 k PLCL blends have low toxicity and can be safely used as an implanted tissue treatment barrier material.

An accurate in-vivo animal model for wound inhibition should produce consistent and reproducible mesothelial injury and ischemia. Forceful abrasion of serosal tissue lining the abdominal cavity and cecal ligation have been previously used to induce adhesions.[45] Though more directly related to operative conditions, abrasion models are largely subjective as the amount of force applied by the operator can vary. Therefore, a cecal ligation mouse model was adopted as the procedure greatly reduces variability in creation of local tissue ischemia via mesenteric and mesothelial disruption. After cecal ligation, mice were randomized and treated with either saline (negative control), Seprafilm® (clinical control), or SBS 40 k/5 k or 40 k PLCL polymer (treatment groups). Adhesion formation and wound healing response were assessed after 7 days. Mice that did not undergo laparotomy and cecal ligation were also assessed as a no wound control.

Figure 8:
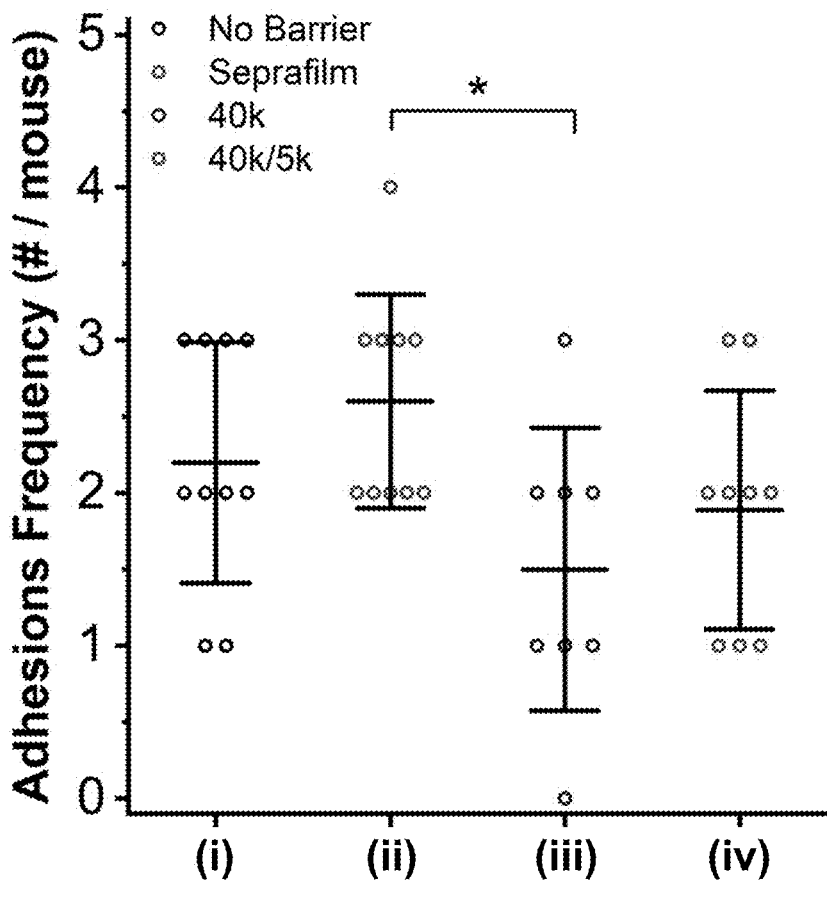
FIG. 8. Total number of adhesions per mouse for (i) no barrier, (ii) Seprafilm®, and (iii) and (iv) poly(L-lactide-co-caprolactone) (PLCL) treated groups post-cecal ligation at t=7 days. Data is plotted as mean±s.e. Asterisks indicate statistical significance: * p<0.05.

A surgeon, blinded to the treatment group, assessed efficacy of SBS deposited fiber mats as adhesion barriers using a Mazuji-derived scoring rubric of clinical severity (FIG. 4B). 40 k/5 k PLCL blends significantly reduced adhesion severity versus No Barrier and Seprafilm® treated controls (FIG. 4C-D), while neat 40 k PLCL did not exhibit the same effect. Additionally, adhesions in 40 k/5 k PLCL treated groups were more frequently described as localized and sealed off from the surrounding space in blinded assessment, with fewer involved organ systems and amassed pockets of inflammatory exudate versus the 40 k PLCL treatment group (FIG. 8). Such a contrast in adhesions prevention efficacy between the two polymer groups versus control groups is likely attributable to differences in biodegradation profiles (FIG. 2C) and tensile strength (FIG. 3A). PLCL 40 k/5 k balances cohesive strength and strong tissue adhesion at the site of injury with rapid erosion, which mitigates the adherence of cells and fibrin that lead to formation of adhesions.

Figure 9:
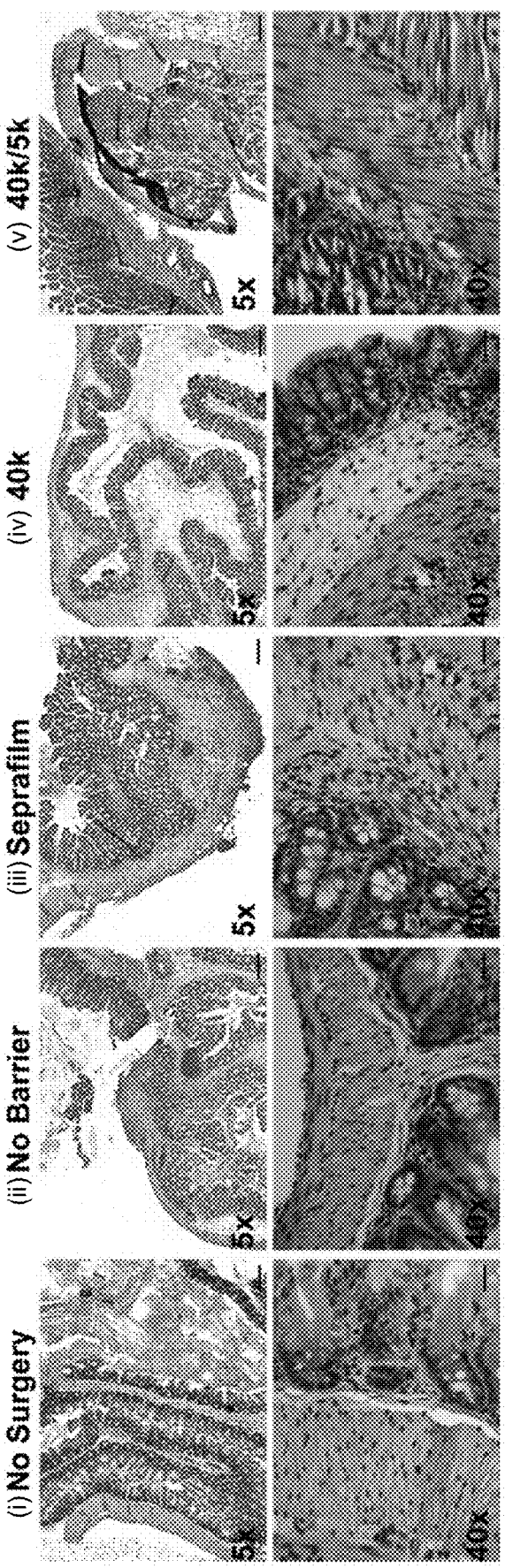
FIG. 9. Additional histological cross sections of mouse cecum for (i) no surgery, (ii) no barrier, (iii) Seprafilm®, and (iv and v) poly(L-lactide-co-caprolactone) (PLCL) treated groups post-cecal ligation at t=7 days. Scale bars=200 μm (top row) and 20 μm (bottom row).

Since fibrin deposition and remodeling is a process regulated by pro-inflammatory signaling molecules,[46,47] cecal tissue was extracted from the mice at Day 7 for analysis of gene expression and histology. Histologic evidence of inflammation, which coincides with adhesion formation, or healing can be used to corroborate assessments of adhesion score severity. Hematoxylin and eosin (H&E) stained cecum displayed infiltration of neutrophils and eosinophils throughout the entire intestinal wall in all cecal ligation groups (FIG. 5A-B, FIG. 9). Quantitative measurements of gross inflammation further assessed via cellularity analysis did not demonstrate significant differences between saline, Seprafilm®, and polymer groups, though all cecal ligation groups displayed increased cellularity compared with the "no surgery" group, as expected.

Figure 10:
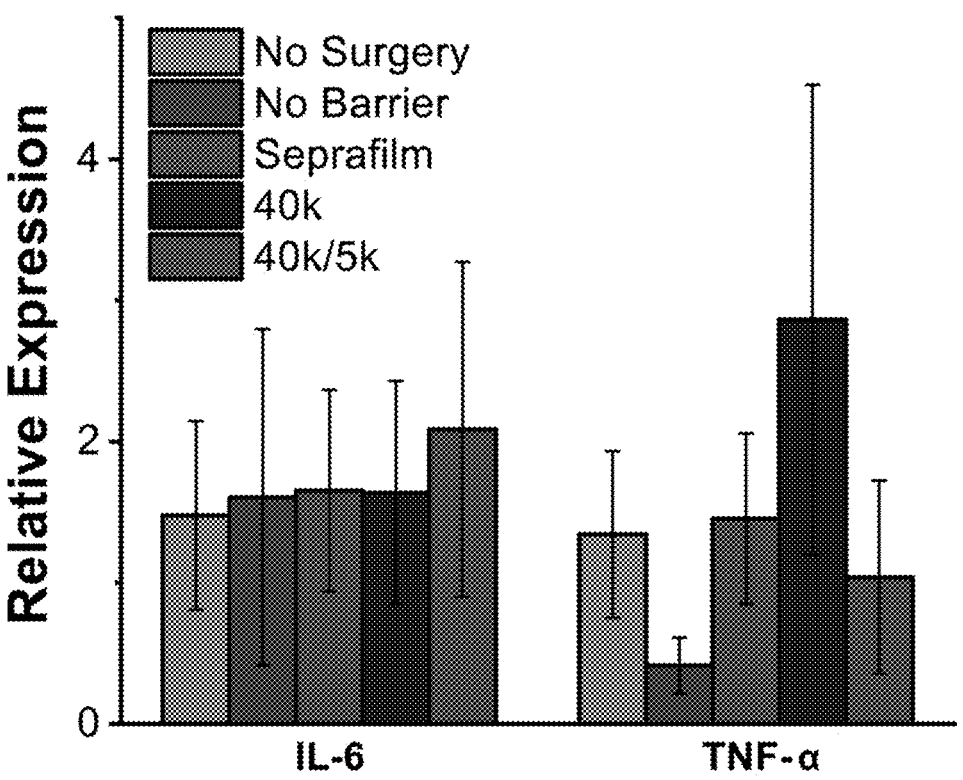
FIG. 10. mRNA expression levels measured via RT-PCR of interleukin-6 (IL-6) and tumor necrosis factor-α (TNF-α) for no surgery, no barrier, Seprafilm®, and poly(L-lactide-co-caprolactone) (PLCL) treated groups post-cecal ligation at t=7 days (n=4-5). Data is plotted as mean±s.e. Asterisks indicate statistical significance: * p<0.05; p<0.01; *p<0.001.

Expression of wound healing genes in IL-6, TNF-α, VEGF-A, TGF-β1, FGF-2, collagen I, collagen III, and IL-1β were measured for ligated cecum samples after 7 days via real-time PCR and compared to tissue from normal ("no surgery") mice (FIG. 5C, FIG. 10). Levels of angiogenic growth factors (VEGF-A) were significantly reduced in the polymer groups versus Seprafilm®. Fibrogenic (TGF-β1 and FGF-2) growth factors exhibited reduced expression in all cecal ligation groups versus the normal "no surgery" group. Levels of collagen I and III expression were decreased in the Seprafilm® and polymer groups versus the no barrier saline group. Collagen I to Collagen III ratio is an indicator of scar-forming collagen prevalent in cases of severe adhesions and was significantly elevated in no barrier saline and Seprafilm® treated groups versus normal controls (FIG. 5D).

Figure 3:
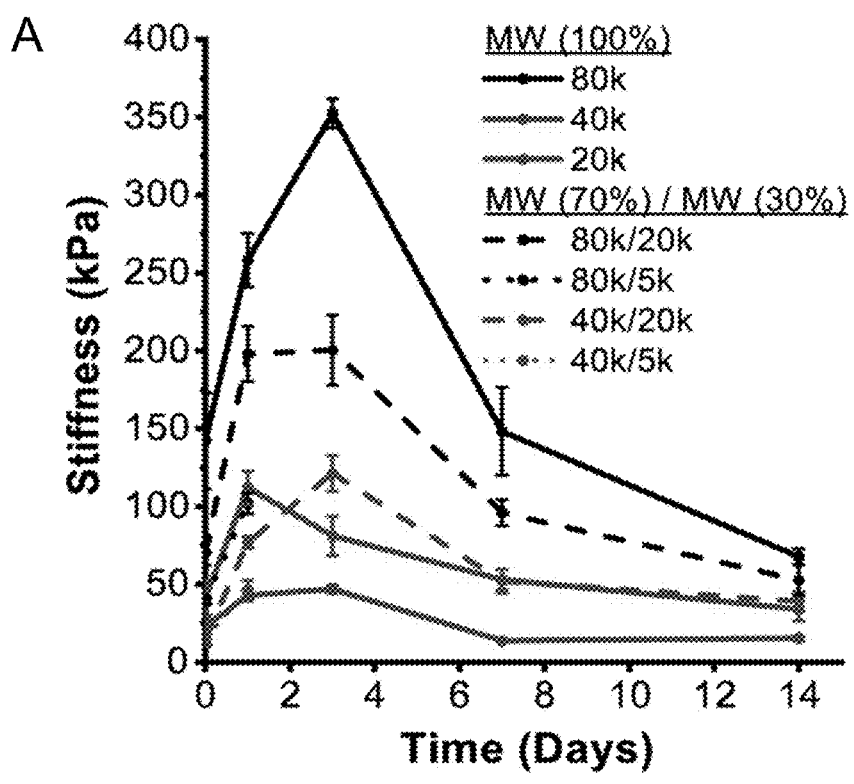
FIG. 3. Graphs showing (A) tensile stiffness, (B) yield strain, and (C) day 0 pull-apart adhesion strength for (i) band-aid-to-skin-tissue and (ii) cardiac-patch-to-intestine-tissue of neat and blend poly(L-lactide-co-caprolactone) (PLCL) during in-vitro degradation. MW=molecular weight. Both pull-apart adhesion tests were done with 1 min of applied pressure, as to show the positive effect on tissue adherence with blending 20 k or 5 k PLCL. Data is plotted as mean±s.e. Asterisks indicate statistical significance: * p<0.05; p<0.01; *p<0.001.
Figure 3:
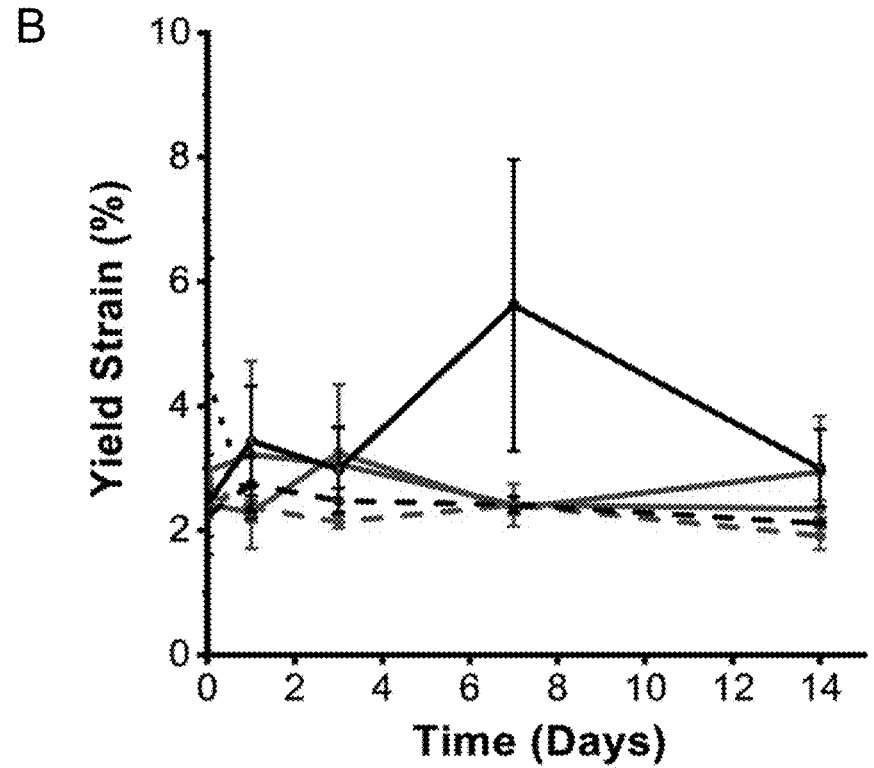
Figure 3:
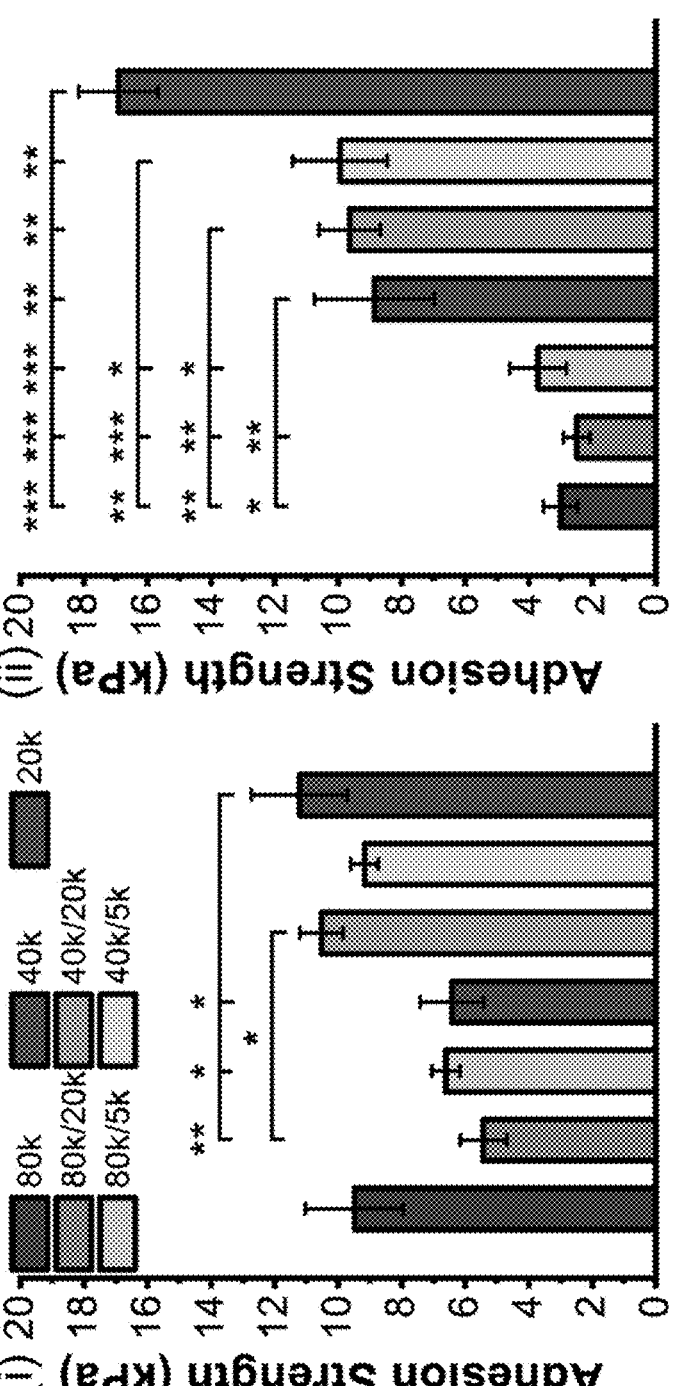

It will be recognized from the foregoing examples that the presently described sprayable "no touch" fiber deposition with SBS addresses practical concerns about imprecise application that surgeons encounter with previously available clinical adhesion barriers. Flexible and viscoelastic PLCL blends address further concerns about brittleness and durability. A biocompatible (FIG. 4A) 40 k/5 k PLCL molecular weight blend yields a barrier that is not only a surface eroding material with an equivalent degradation rate over 14d tuned to fibrotic scar tissue deposition (FIG. 2C), but also improved wet tissue adherence and tensile elasticity when compared with neat high molecular weight components (FIG. 3).

Advantages of the described solid adhesion barriers include but are not necessarily limited to an ability to withstand dynamic shear forces frequently present in-vivo due to intestinal peristalsis or shifting of organs. Hydrogel based clinical barriers such as Seprafilm® are hydrophilic and present surface properties capable of delaying a fibrotic response via reduction of tissue-tissue contact time. Seprafilm® was chosen as the clinical control for in-vivo studies. However, these cellulose-derived dressings are inherently brittle prior to swelling due to their crystallinity, and lose significant adhesive and cohesive strength after swelling.[19,20] Additionally, Seprafilm® and other synthetic hydrogel-based materials may impede wound healing and are especially difficult to use in abdominal surgery, resulting in limited usability in clinical settings.[21-24]

Both neat 40 k and 40 k/5 k blend compositions of PLCL exhibited an ability to reduce abdominal adhesions severity in a cecal ligation mouse model versus no barrier saline and Seprafilm® controls, with 40 k/5 k in particular demonstrating statistical significance (FIG. 4C-D). In addition to having less-severe adhesive disease as denoted by the clinical scoring rubric (FIG. 4B), mice treated with polymer had a decreased overall level of inflammation, as qualified through visible accumulation of inflammatory exudate by a blinded surgeon during clinical assessment. Though polymer groups were scored as having less-severe disease when compared with the current FDA-approved adhesion barrier Seprafilm®, analysis of the gene expression of collagens I and III demonstrated equivalence between the Seprafilm® and polymer groups with respect to wound healing extent, as all three groups displaying decreased levels versus no barrier saline controls (FIG. 5).

Figure 5:
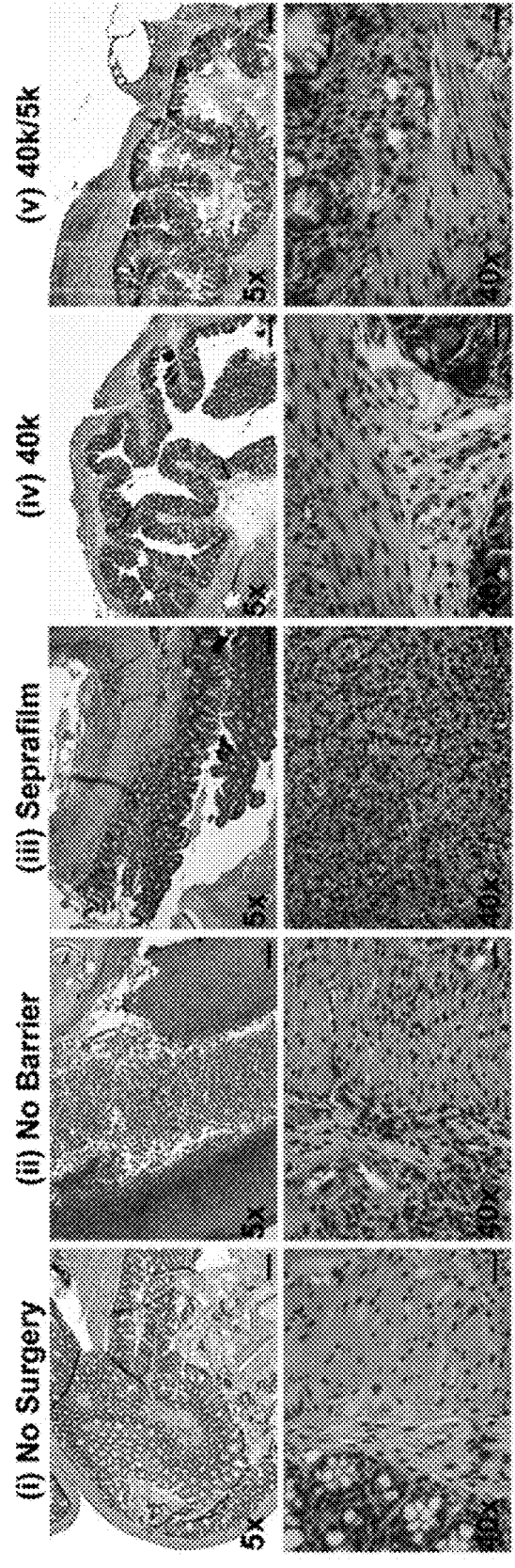
FIG. 5. Histological cross sections (A) and cellularity of mouse cecum (B), and (C) mRNA expression levels measured via RT-PCR of vascular endothelial growth factor (VEGF-A), transforming growth factor-β1 (TGF-β1), fibroblast growth factor-2 (FGF-2), collagen I (COL1), collagen III (COL3), and interleukin-1β (IL-1β) wound healing gene markers and (D) ratio of collagen I to collagen III expression for (i) no surgery, (ii) no barrier, (iii) Seprafilm®, and (iv and v) poly(L-lactide-co-caprolactone) (PLCL) treated groups post-cecal ligation at t=7 days (n=4-5). Scale bars=200 μm (top row) and 20 μm (bottom row). Data is plotted as mean±s.e. Asterisks indicate statistical significance: * p<0.05; p<0.01; *p<0.001.
Figure 5:
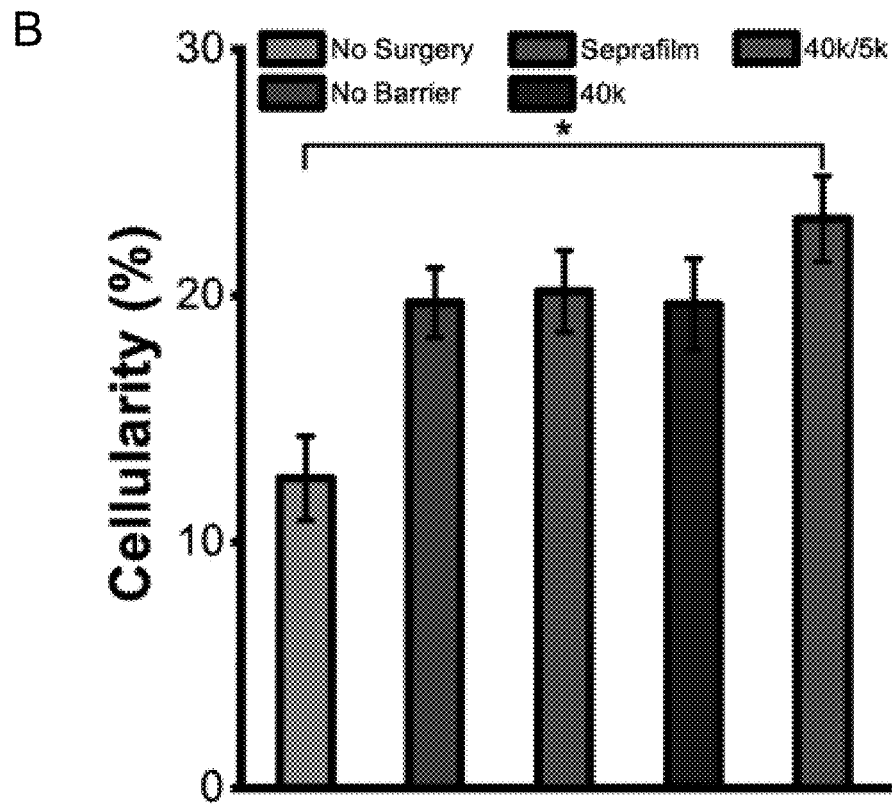
Figure 5:
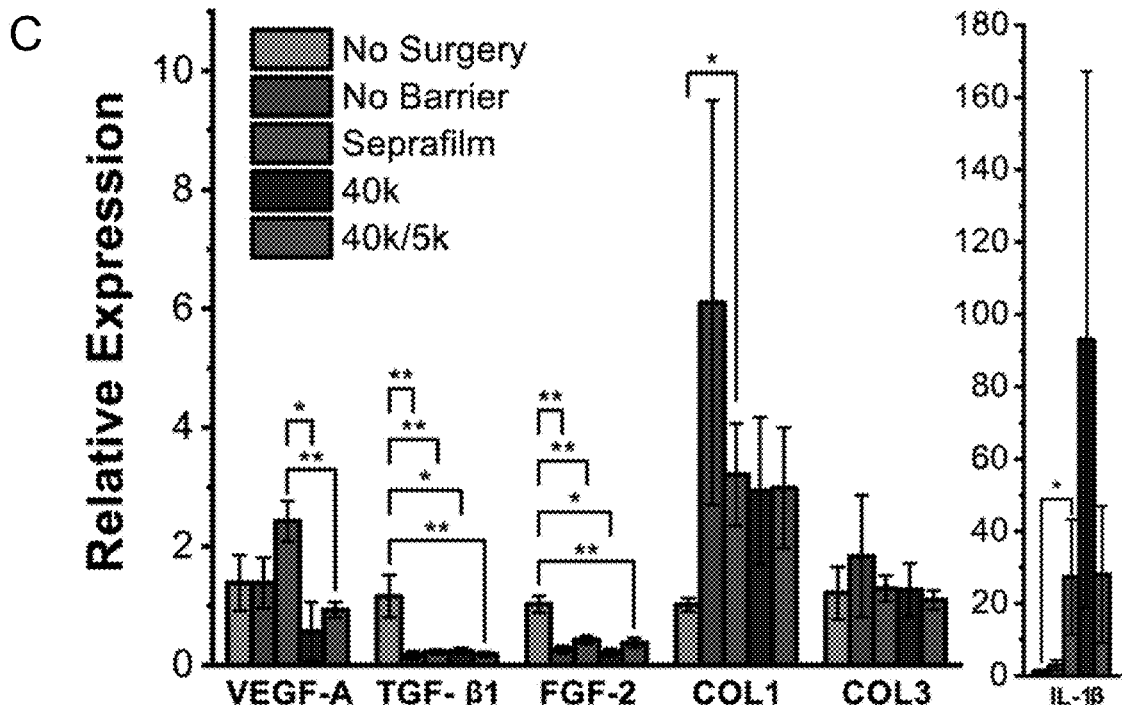
Figure 5:
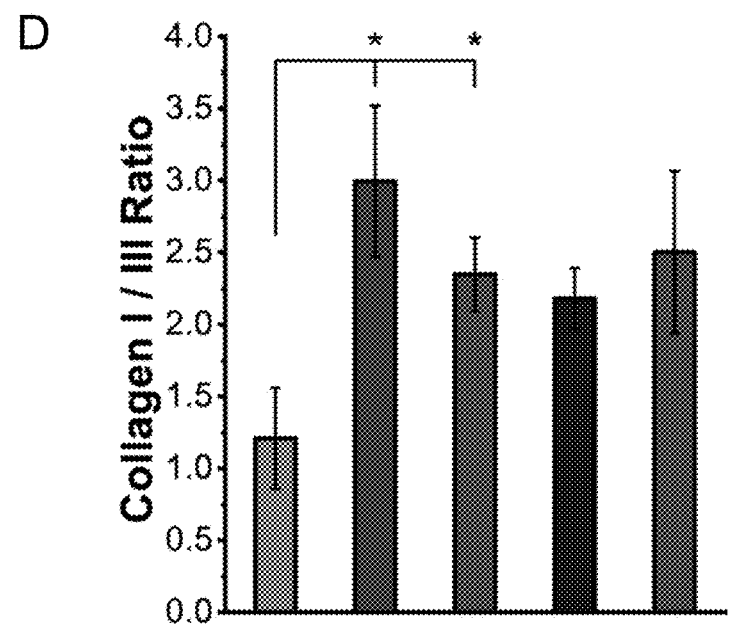

Extent of fibrosis was assessed via histology and quantification of wound healing gene expression, where expression levels across controls and treatment groups were similar, with the exception of a significant decrease in angiogenic growth factor VEGF-A for 40 k/5 k blend PLCL versus no barrier and Seprafilm® controls (FIG. 5).

Example 3—Materials and Methods 1.1 Polymer Solution Preparation

Polymer solutions were prepared at a 20% (w/v) concentration in ethyl acetate for polymers characterized in-vitro and in-vivo. When used in its pure liquid form, ethyl acetate is regarded as a Class 3 solvent with low toxic potential by the U.S. Food and Drug Administration and the International Council for Harmonisation of Technical Requirements for Pharmaceuticals for Human Use, hence the selection of ethyl acetate in all datasets.[32,48] Both neat polymer solutions and blends comprised of neat poly(D,L-lactide-co-caprolactone) were investigated for "low" molecular weight (LMW) compositions terminologically defined as 5 k PLCL (70:30 L:CL, acid endcap, Mn 1,000-5,000 Da, Akina) or 20 k PLCL (70:30 L:CL, acid endcap, Mn 15,000-25,000 Da, Akina), and "high" molecular weight (HMW) compositions defined as 40 k PLCL (70:30 L:CL, acid endcap, Mn 35,000-45,000 Da, Akina) or 80 k PLCL (70:30 L:CL, acid endcap, Mn 75,000-85,000 Da, Akina). Polymer blends were mixed in a 70:30 mass ratio for a total of four blends of 1) 80 k/20 k, 2) 80 k/5 k, 3) 40 k/20 k, and 4) 40 k/5 k, where the leading component in the abbreviation is the majority (i.e., 70%) component of the blend and the secondary component is in minority (i.e., 30%). An airbrush (Master Airbrush, G222-SET, 0.2 mm nozzle diameter) was used to deposit the solutions as dry, conformal polymer fibers. The airbrush was connected to a compressed $CO_2$ tank equipped with a pressure regulator set to 20 psig.

1.2 Mass Loss and Degradation Testing

Polymer samples were produced by solution blow spinning (SBS) onto a 22 mm by 22 mm glass coverslip, with the distance between airbrush nozzle and cover slip at approximately 10 cm. Polymer samples for mass loss studies were produced by spraying 2 mL of polymer solution onto a coverslip. A microbalance (Sartorius ME-5) was used to determine the net increase in mass after the spinning process was complete, which is defined as the initial sample mass, $m_i$. Samples submerged in 4 mL of 1×PBS in wells of a 6-well plate and stored in a shaker incubator at 37° C. and 100 rpm. Samples were removed at time points of 1, 3, 7, and 14 days. At these points, the PBS was removed, and the samples were stored in a vacuum desiccator for three days. The samples were weighed again to determine the final mass, $m_f$, and mass loss ($m_i-m_f$) was calculated as a percentage of $m_i$. Five samples were used for each time point and polymer composition (n=5).

1.3 Gel Permeation Chromatography

Polymer samples from time points of degradation (1, 3, 7, 14 days) and non-degraded samples (i.e., 0 days) were dissolved at 3 mg ml$^{-1}$ in tetrahydrofuran (THF). Samples were run on the Waters e2695 Separations Module with Waters 2414 Refractive Index Detector, and Waters HSPgel columns in series (HR MB-L and HR 3.0 columns, 6.0 mm I.D.×15 cm). Molecular weight is reported as polystyrene relative molecular weight, as calculated from a 10-point calibration curve generated using Agilent EasiCal polystyrene standards dissolved at 2 mg mL$^{-1}$ in THF. GPC analysis was performed using Waters Empower 3 Chromatography Data software. The weight-average molecular weight, number-average molecular weight, and polydispersity of each sample were then obtained from the sample curves and recorded. Each sample type was replicated 3 times (n=3).

1.4 Tensile Strength Testing

Tensile strength testing was performed to determine the mechanical properties of the polymer samples over time. For the 0-day (i.e., non-degraded) experiment, samples were produced by spraying 2 mL of polymer solution onto a glass coverslip. For 1, 3, 7, and 14-day timepoints, polymer samples were degraded according to the procedure described in the degradation testing section, removed from the coverslips, and trimmed to a rectangular shape approximately 10 mm by 5 mm in size. Exact sample dimensions were measured immediately prior to testing. Tensile testing was performed on a TA Instruments DMA Q800 equipped with a film tensile clamp. Samples were stretched under a controlled force ramp from 0 N to 5 N at a rate of 0.01 N min$^{-1}$ and measurements made at room temperature. Elastic modulus was calculated from the linear region of the resulting stress versus strain curve, with a 0.2% offset used to calculate sample yield stress and strain. Each sample type was replicated 5 times (n=5).

1.5 Pull-Apart Adhesion Testing

Pull-apart testing was performed on the TA Instruments DMA Q800. For testing on porcine skin, CVS Health Plastic One-Size Bandages were placed in baths of ethanol to remove the adhesive. For testing on porcine intestine, Gore- Tex Cardiovascular Patch (polytetrafluoroethylene, Gore Medical) were used as is. Both types of substrate material were cut into 8 mm square segments with 1 mL of polymer solution sprayed onto each, and 1 mL sprayed onto one or more sections of either porcine skin or intestine. Polymer coated band-aids and cardiac patch sections were allowed to set for 15 minutes in 37° C. ambient air. Square sections of 8 mm frozen porcine skin or intestine were cut and warmed to room temperature by coating the tissue in water and letting the tissue warm for 10 minutes in 37° C. ambient air. Warmed polymer coated substrates were brought into contact with porcine skin or intestine and superglued to the clamps of the dynamic mechanical analyzer in compression mode—the porcine skin to the fixed clamp and the polymer coated or uncoated band-aid to the movable clamp. The samples were compressed at 1 N for 5 min and after this compression period a controlled force ramp was used to increase pull-apart force at a rate of 1 N min$^{-1}$ until failure. The adhesion strength of each sample was recorded. Each sample type was replicated five times (n=5).

1.6 Cell Viability

Cytotoxicity of polymer compositions was tested against L929 mouse fibroblasts by an elution method as described by ISO-10993-5.[49] 40 k/5 k PLCL blend and neat 40 k PLCL and 5 k PLCL compositions were sprayed onto sterile 22 mm by 22 mm glass coverslips. The polymer mats were then removed from the coverslips and eluted at mass concentration of 10 mg/mL in culture media of Dulbecco's modified Eagle medium supplemented with 10% fetal bovine serum (Gemini Bio-Products Inc.), L-glutamine and 1% penicillin and streptomycin at standard conditions (37° C., 5% $CO_2$) for 24 hours. The elutions were diluted to 1×, 10×, and 100× dilutions, and cell viability was tested against the different dilutions.

L929 fibroblasts (105 cells/mL) were plated into 96-well plates at 100 uL per well and incubated for 24 hours under standard conditions. The culture media was removed by pipette. Finally, wells were then treated to control (standard media), 25 ug/mL puromycin, or diluted elutions of 40 k/5 k PLCL blend, neat 40 k PLCL, and neat 5 k PLCL compositions. This measurement was repeated five times for each diluted elution (n=5).

1.7 Mouse Cecal Ligation Adhesions Model

All animal procedures were approved by the Children's National Hospital Institutional Animal Care and Use Committee (IACUC protocol #000030703), and the animals were treated in accordance with PHS Policy on Humane Care and Use of Laboratory Animals, the National Institute of Health Guide for the Care and Use of Laboratory Animals, and the Animal Welfare Act. Forty, 7-15-week-old C57BL/6 female mice were used (Jackson Laboratory). Mice were randomized into groups based on the treatment group. Normal saline injection was used as a negative control, while Seprafilm® (Genzyme) was used as an anti-adhesion, clinical control. Experimental endpoint was 7 days after surgery with a total of five mice (n=5) allocated per group. Polymer solutions of 40 k/5 k PLCL blend and neat 40 k PLCL were made under sterile conditions in a biosafety cabinet, and later sterilized by UV irradiation in their respective vials. Prior to surgery, a dedicated airbrush was sterilized with ethanol and placed under UV radiation along with polymer solutions.

All mice were anesthetized with a 100 mg kg-1 ketamine and 10 mg kg-1 xylazine solution (0.1 mL/10 g mouse mass). After anesthesia, the mice were positioned supine, and skin prepped with betadine solution. In sterile fashion, a 1 cm laparotomy incision was made at the midline. After dissection into the abdominal cavity, the cecum was exposed and ligated with 4-0 Vicryl® Suture (Ethicon) approximately 1 cm from distal end. In the case of normal saline injection, cecum was placed back into the abdominal cavity and 0.1 mL sterile saline was dripped onto ligated cecum. For the Seprafilm® control group, the cecum was placed back into the abdominal cavity and a 1 cm square section gently placed on top of ligated cecum. For polymer treatment groups, 0.5 mL of solution was sprayed onto a ligated cecum prior to replacement in the abdominal cavity. Upon reinsertion of cecum, skin was closed using 4-0 Vicryl® Suture (Ethicon) in a running fashion, and approximately 0.1 mL buprenorphine was given as an analgesic at the end of the surgery.

Each animal was weighed both pre-operatively and at 7 days after initial surgery prior to euthanasia. Midline laparotomy was performed post-euthanasia, and images of the abdominal cavity were taken with a camera. The abdominal space was then examined by a surgeon who was blinded to treatment groups and assessed for adhesions formation with scores on a Mazuji-derived scale assigned to each attached organ pair, as well as signs of inflammation and degradation of the polymer sample.[50]

1.8 Histological Analysis

Ligated cecum tissues were harvested on postoperative day 7 and kept in 10% neutral buffered formalin until histological processing (Histosery Inc.), then embedded in paraffin wax. Five μm sections were prepared, fixed onto glass slides, and stained with hematoxylin and eosin (H&E). Digital images of the histology slides were taken with TissueScope LE (Huron Digital Pathology) at 5× and 40× magnification then the 40× images were exported for analysis intestinal wall cellularity. One section per mouse, with 5 separate low-powered and high-powered fields of view were imaged per section. Using ImageJ (National Institutes of Health), images were scaled to 1 μm/pixel and converted to an RGB stack. A threshold of 100 was set, and the percent area of the image stained purple was obtained for each image. These percentages were then averaged for each mouse.

1.9 Wound Healing Gene Expression

RNA was extracted from frozen cecal tissue using Trizol reagent (Life Technologies, Frederick, MD). In all experiments, 6 μg RNA was used to synthesize first strand cDNA using High-Capacity cDNA Reverse Transcription Kit (Life Technologies). Real-time PCR was performed using TaqMan® Gene Expression Master Mix (Life Technologies) in a QuantStudio7 Flex RT-PCR system (Thermo Fisher Scientific, Waltham, MA), according to the manufacturer's instructions. Reactions were performed in triplicate, including no template and endogenous control using GAPDH. Gene-specific assays were Mm00434228_m1 for Il1b, Mm0046190_m1 for Il6, Mm00443258_m1 for Tnfa, Mm00437306_m1 for Vegfa, Mm01178820_m1 for Tgfb1, Mm00433287_m1 for Fgf2, Mm00801666_g1 for Col1a1, Mm00802305_g1 for Col3a 1, and Mm99999915_g1 for Gapdh (Life Technologies, Thermo Fisher). Changes in relative gene expression normalized to GAPDH levels were determined using the ΔΔCt method. First, the difference between the Ct values (ΔCt) of the gene of interest and the housekeeping gene was calculated for each sample. Then the ΔCt values for the control samples were averaged. The difference in the ΔCt values between each experimental sample and the control sample (ΔΔCt) was calculated. The fold-change in expression of the gene of interest compared to the housekeeping gene for each sample was calculated as $2^{-\Delta\Delta Ct}$, and the results were averaged for graphical representation.

1.10 Contact Angle

Surface wettability was characterized by water contact angle measurements at room temperature, with images captured on a Sony a7R IV D3400 (Sony) and subsequent analysis performed in ImageJ (National Institutes of Health). Non-degraded (Day 0) and degraded polymer samples (Day 14) were prepared as described above. Advancing contact angle of 10 μL droplets of deionized (DI) water was measured using the sessile drop technique. Five samples were used for each polymer composition and time point (n=5).

1.11 Statistical Analysis

Statistical analysis was performed on Origin (OriginLab). Typically, one-way ANOVA was used to compare group variation, followed by post-hoc pairwise Tukey comparison to determine significant differences between the groups. Typically, averages were plotted with error bars representing standard error. Asterisks are used to indicate statistically significant differences: $*=P<0.05$, $=P<0.01$, $*=P<0.001$. If no asterisks are shown, there are no significant differences amongst the groups. Real-time PCR results were analyzed using t-tests comparing the $\Delta\Delta Ct$ values.

References—This reference listing is not an indication that reference is material to patentability.

ADDIN ZOTERO_BIBL {"uncited":[ ],"omitted":[ ],"custom":[ ] } CSL_BIBLIOGRAPHY 1. Cheong Y C, Laird S M, Li T C, Shelton J B, Ledger W L, Cooke I D. Peritoneal healing and adhesion formation/reformation. *Human Reproduction Update.* 2001; 7(6):556-566. doi: 10.1093/humupd/7.6.556

2. Monk B J, Berman M L, Montz F J. Adhesions after extensive gynecologic surgery: Clinical significance, etiology, and prevention. *American Journal of Obstetrics and Gynecology.* (5).

3. Kamel R M. Prevention of postoperative peritoneal adhesions. *European Journal of Obstetrics & Gynecology and Reproductive Biology.* 2010; 150(2): 111-118. doi: 10.1016/j.ejogrb.2010.02.003

4. diZerega G S. Peritoneal repair and post-surgical adhesion formation. *Human Reproduction Update.* 2001; 7(6):547-555. doi: 10.1093/humupd/7.6.547

5. Arung W, Meurisse M, Detry O. Pathophysiology and prevention of postoperative peritoneal adhesions. *WJG.* 2011; 17(41). doi:10.3748/wjg.v17.i41.4545

6. Attard J A P, MacLean A R. Adhesive small bowel obstruction: epidemiology, biology and prevention. 50(4).

7. diZerega G S. Biochemical events in peritoneal tissue repair. *Eur J Surg Suppl.* 1997; (577): 10-16.

8. Menzies D. Postoperative adhesions: their treatment and relevance in clinical practice. *Ann R Coll Surg Engl.* 1993; 75(3):147-153.

9. Menzies D. Peritoneal adhesions. Incidence, cause, and prevention. *Surg Annu.* 1992; 24 Pt 1:27-45.

10. Moscowitz I, Wexner S D. Contributions of Adhesions to the Cost of Healthcare. In: diZerega G S, ed. *Peritoneal Surgery.* Springer New York; 2000:335-342. doi:10.1007/978-1-4612-1194-5_30

11. Menzies D, Ellis H. Intestinal obstruction from adhesions—how big is the problem? *Ann R Coll Surg Engl.* 1990; 72(1):60-63.

12. Butureanu S A, Butureanu T A S. Pathophysiology of adhesions. *Chirurgia (Bucur).* 2014; 109(3):293-298.

13. Ward B C, Panitch A. Abdominal Adhesions: Current and Novel Therapies. *Journal of Surgical Research.* 165 (1):91-111. doi:10.1016/j.jss.2009.09.015

14. Gutt C N, Oniu T, Schemmer P, Mehrabi A, Michler M W. Fewer adhesions induced by laparoscopic surgery? *Surg Endosc.* 2004; 18(6): 898-906. doi: 10.1007/s00464-003-9233-3

15. Vrijland W W, Jeekel J, van Geldorp H J, Swank D J, Bonjer H J. Abdominal adhesions: intestinal obstruction, pain, and infertility. *Surg Endosc.* 2003; 17(7):1017-1022. doi:10.1007/s00464-002-9208-9

16. Ray N. Abdominal Adhesiolysis: Inpatient Care and Expenditures in the United States in 1994. *Journal of the American College of Surgeons.* 1998; 186(1):1-9. doi: 10.1016/S1072-7515(97)00127-0

17. Sikirica V, Bapat B, Candrilli S D, Davis K L, Wilson M, Johns A. The inpatient burden of abdominal and gynecological adhesiolysis in the US. *BMC Surg.* 2011; 11(1):13. doi:10.1186/1471-2482-11-13

18. Ellis H. The clinical significance of adhesions: focus on intestinal obstruction. *Eur J Surg Suppl.* 1997; (577):5-9.

19. Diamond M P, Burns E L, Accomando B, Mian S, Holmdahl L. Seprafilm® adhesion barrier: (1) a review of preclinical, animal, and human investigational studies. *Gynecol Surg.* 2012; 9(3):237-245. doi: 10.1007/s10397-012-0741-9

20. Diamond M P, Burns E L, Accomando B, Mian S, Holmdahl L. Seprafilm® adhesion barrier: (2) a review of the clinical literature on intraabdominal use. *Gynecol Surg.* 2012; 9(3):247-257. doi:10.1007/s10397-012-0742-8

21. Klingler P J, Floch N R, Seelig M H, Branton S A, Wolfe J T, Metzger P P. Seprafilm®-induced peritoneal inflammation: A previously unknown complication: Report of a case. *Diseases of the Colon & Rectum.* 1999; 42(12): 1639-1642. doi:10.1007/BF02236221

22. Vrijland W W, Tseng L N L, Eijkman H J M, et al. Fewer Intraperitoneal Adhesions With Use of Hyaluronic Acid—Carboxymethylcellulose Membrane: A Randomized Clinical Trial. *Annals of Surgery.* 2002; 235(2):193-199. doi:10.1097/00000658-200202000-00006

23. Mohri Y, Uchida K, Araki T, et al. Hyaluronic Acid—Carboxycellulose Membrane (Seprafilm) Reduces Early Postoperative Small Bowel Obstruction in Gastrointestinal Surgery. *The American Surgeon.* 2005; 71(10):861-863. doi:10.1177/000313480507101014

24. Beck D E, Cohen Z, Fleshman J W, Kaufman H S, van Goor H, Wolff B G. A Prospective, Randomized, Multicenter, Controlled Study of the Safety of Seprafilm® Adhesion Barrier in Abdominopelvic Surgery of the Intestine. *Diseases of the Colon & Rectum.* 2003; 46(10):1310-1319. doi:10.1007/s10350-004-6739-2

25. Stapleton L M, Steele A N, Wang H, et al. Use of a supramolecular polymeric hydrogel as an effective postoperative pericardial adhesion barrier. *Nat Biomed Eng.* 2019; 3(8):611-620. doi:10.1038/s41551-019-0442-z 26. Stapleton L M, Lucian H J, Grosskopf A K, et al. Dynamic Hydrogels for Prevention of Post-Operative Peritoneal Adhesions. *Adv Therap.* 2021; 4(3):2000242. doi:10.1002/adtp.202000242

27. Bachmann B, Spitz S, Schädl B, et al. Stiffness Matters: Fine-*Tuned Hydrogel Elasticity* Alters Chondrogenic Redifferentiation. *Front Bioeng Biotechnol.* 2020; 8:373. doi:10.3389/fbioe.2020.00373

28. Prager J, Adams C F, Delaney A M, et al. Stiffness-matched biomaterial implants for cell delivery: clinical, intraoperative ultrasound elastography provides a 'target' stiffness for hydrogel synthesis in spinal cord injury. *J Tissue Eng.* 2020; 11:204173142093480. doi:10.1177/2041731420934806

29. Huang G, Wang L, Wang S, et al. Engineering three-dimensional cell mechanical microenvironment with hydrogels. *Biofabrication.* 2012; 4(4):042001. doi: 10.1088/1758-5082/4/4/042001

30. Taboada G M, Yang K, Pereira M J N, et al. Overcoming the translational barriers of tissue adhesives. *Nat Rev Mater.* 2020; 5(4):310-329. doi:10.1038/s41578-019-0171-7

31. Nam S, Mooney D. Polymeric Tissue Adhesives. *Chem Rev.* 2021; 121(18):11336-11384. doi:10.1021/acs.chemrev.0c00798

32. Daristotle J L, Lau L W, Erdi M, et al. Sprayable and biodegradable, intrinsically adhesive wound dressing with antimicrobial properties. *Bioeng Transl Med.* 2020; 5(1). doi:10.1002/btm2.10149

33. Behrens A M, Lee N G, Casey B J, et al. Biodegradable-Polymer-Blend-Based Surgical Sealant with Body-Temperature-Mediated Adhesion. *Adv Mater.* 2015; 27(48):8056-8061. doi:10.1002/adma.201503691

34. Behrens A M, Casey B J, Sikorski M J, et al. In Situ Deposition of PLGA Nanofibers via Solution Blow Spinning. *ACS Macro Lett.* 2014; 3(3):249-254. doi:10.1021/mz500049x 35. Kern N G, Behrens A M, Srinivasan P, et al. Solution blow spun polymer: A novel preclinical surgical sealant for bowel anastomoses. *Journal of Pediatric Surgery.* 2017; 52(8):1308-1312. doi:10.1016/j.jpedsurg.2016.11.044

36. Daristotle J L, Zaki S T, Lau L W, et al. Improving the adhesion, flexibility, and hemostatic efficacy of a sprayable polymer blend surgical sealant by incorporating silica particles. *Acta* Biomaterialia. 2019; 90:205-216. doi: 10.1016/j.actbio.2019.04.015

37. Daristotle J L, Zaki S T, Lau L W, et al. Pressure-Sensitive Tissue Adhesion and Biodegradation of Viscoelastic Polymer Blends. *ACS Appl Mater Interfaces.* 2020; 12(14):16050-16057. doi:10.1021/acsami.0c00497

38. Daristotle J L, Erdi M, Lau L W, et al. Biodegradable, *Tissue Adhesive Polyester Blends for* Safe, Complete Wound Healing. *ACS Biomater Sci Eng.* 2021; 7(8):3908-3916. doi: 10.1021/acsbiomaterials.1c00865

39. Jesmer A H, Wylie R G. Controlling Experimental Parameters to Improve Characterization of Biomaterial Fouling. *Front Chem.* 2020; 8:604236. doi:10.3389/fchem.2020.604236

40. Yu J. Biodegradation-based Polymer Surface Erosion and Surface Renewal for Foul-release at Low Ship Speeds. *Biofouling.* 2003; 19(sup1):83-90. doi:10.1080/0892701031000063820

41. Peppas N A, Buri P A. Surface, interfacial and molecular aspects of polymer bioadhesion on soft tissues. *Journal of Controlled Release.* 1985; 2:257-275. doi:10.1016/0168-3659(85)90050-1

42. Felton L. Influence of plasticizers on the adhesive properties of an acrylic resin copolymer to hydrophilic and hydrophobic tablet compacts. *International Journal of Pharmaceutics.* 1997; 154(2):167-178. doi:10.1016/S0378-5173(97)00133-6

43. Kinloch A J. The science of adhesion. *Journal of Materials Science.* 1980; 15(9):2141-2166. doi:10.1007/BF00552302

44. Taylor M S, Daniels A U, Andriano K P, Heller J. Six bioabsorbable polymers: In vitro acute toxicity of accumulated degradation products. *J App Biomater.* 1994; 5(2):151-157. doi:10.1002/jab.770050208

45. Oncel M, Remzi F H, Connor J, Fazio V W. Comparison of cecal abrasion and multiple-abrasion models in generating intra-abdominal adhesions for animal studies. *Tech Coloproctol.* 2005; 9(1):29-33. doi:10.1007/s10151-005-0189-2

46. Caetano G F, Fronza M, Leite M N, Gomes A, Frade MAC. Comparison of collagen content in skin wounds evaluated by biochemical assay and by computer-aided histomorphometric analysis. *Pharmaceutical Biology.* 2016; 54(11):2555-2559. doi:10.3109/13880209.2016.1170861

47. Friedman S. Cytokines and Fibrogenesis. *Semin Liver Dis.* 1999; 19(02):129-140. doi:10.1055/s-2007-1007105

48. *Q3C Impurities: Guideline for Residual Solvents.* The International Council for Harmonisation of Technical Requirements for Pharmaceuticals for Human Use (ICH); 2021:1-7. Accessed Apr. 19, 2022. https://database.ich.org/sites/default/files/ICH_Q3C-R8_Guideline_Step4_2021_0422_1.pdf 49. International Organization for Standardization. ISO 10993-5:2009 *Biological Evaluation of Medical Devices—Part 5: Tests for in Vitro Cytotoxicity.* 3rd ed. International Organization for Standardization; 2009.

50. Mazuji M K. Prevention of Adhesions With Polyvinylpyrrolidone: Preliminary Report. *Arch Surg.* 1964; 89(6):1011. doi:10.1001/archsurg.1964.01320060079015

What is claimed is:

1. A composition consisting essentially of a mixture of 40 k and 5 k poly(L-lactide-co-caprolactone) (PLCL), wherein the 40 k and 5 k PLCL are present in a 70:30 mass ratio, respectively, wherein the composition is free of poly(lactic-co-glycolic acid) (PLGA), poly(ethylene glycol) (PEG) and nanoparticles, and when in contact with a tissue wound the composition is optionally a solid adhesive.

* * * * *